US 8,658,180 B2

(12) United States Patent
Miller et al.

(10) Patent No.: US 8,658,180 B2
(45) Date of Patent: Feb. 25, 2014

(54) VACCINES AGAINST INFLUENZA VIRUS

(76) Inventors: Mark A. Miller, Chevy Chase, MD (US); Rachel Schneerson, Bethesda, MD (US); Joanna Kubler-Kielb, Bethesda, MD (US); John B. Robbins, New York, NY (US); Zuzana Biesova, Rockville, MD (US); Jerry Keith, Olney, MD (US)

(*) Notice: Subject to any disclaimer, the term of this patent is extended or adjusted under 35 U.S.C. 154(b) by 619 days.

(21) Appl. No.: 12/541,804

(22) Filed: Aug. 14, 2009

(65) Prior Publication Data

US 2010/0150954 A1    Jun. 17, 2010

Related U.S. Application Data

(60) Provisional application No. 61/089,384, filed on Aug. 15, 2008.

(51) Int. Cl.
  *A61K 39/00*  (2006.01)
  *A61K 39/38*  (2006.01)
  *A61K 39/12*  (2006.01)
  *A61K 39/385* (2006.01)

(52) U.S. Cl.
  USPC .............. 424/194.1; 424/184.1; 424/185.1; 424/186.1; 424/196.11

(58) Field of Classification Search
  None
  See application file for complete search history.

(56) References Cited

U.S. PATENT DOCUMENTS

| | | |
|---|---|---|
| 2004/0223976 A1 | 11/2004 | Bianchi et al. |
| 2007/0286873 A1 | 12/2007 | Williams et al. |
| 2009/0162400 A1 | 6/2009 | Powell et al. |

FOREIGN PATENT DOCUMENTS

| | | | |
|---|---|---|---|
| WO | WO 92/22318 | 12/1992 | |
| WO | WO 96/37624 | 11/1996 | |
| WO | WO 2006061723 | * 12/2005 | ............ C07K 16/10 |
| WO | WO 2007/067681 | 6/2007 | |
| WO | WO 2007/085969 | 8/2007 | |
| WO | WO 2007/010388 | 9/2007 | |
| WO | WO 2007/103322 | 9/2007 | |
| WO | WO 2008/054540 | 5/2008 | |
| WO | WO 2008/112017 | 9/2008 | |
| WO | WO 2009/029686 | 3/2009 | |
| WO | WO 2009/053535 | 4/2009 | |
| WO | WO 2009/064805 | 5/2009 | |
| WO | WO 2009/162400 | 6/2009 | |

OTHER PUBLICATIONS

Neirynck, et al. A universal influenza A vaccine based on the extracellular domain of the M2 protein. Nat. Med. 1999; 5(10):1157-1163.*

(Continued)

*Primary Examiner* — Jeffrey Stucker
*Assistant Examiner* — Stuart W Snyder
(74) *Attorney, Agent, or Firm* — Klarquist Sparkman, LLP

(57) ABSTRACT

Disclosed are immunogenic conjugates having the general formula:

M2e-Cys-S—$CH_2$—C(O)—NH—$CH_2$—CH2-C(O—)NH-Lys-Pr, were M2e is the influenza M2 ectodomain (M2e) peptide; Cys is a cysteine amino acid residue present in the M2e peptide; S the sulfur present in the cysteine amino acid residue; CH2-CO—NH—CH2-CH2-CO the linking group; NH the amine group present in a lysine residue of the carrier; Lys is a lysine amino acid residue and Pr the carrier protein. Also disclosed are isolated immunogens that include an immunogenic fragment of an influenza HA protein including the polybasic cleavage site, wherein the immunogenic fragment of the influenza HA protein has been modified to remove an N-terminal leader amino acid sequence and a C-terminal transmembrane domain. Also disclosed are methods producing an influenza vaccine specific for an identified influenza strain.

22 Claims, 5 Drawing Sheets

(56) References Cited

OTHER PUBLICATIONS

Mezo, et al. Synthesis and Structural Characterization of Bioactive Peptide Conjugates using Thioether Linkage Approaches. J. Peptide Sci. 2004; 10: 701-713.*

Kossaczka et al. *Vibrio cholerae* O139 Conjugate Vaccines: Synthesis and Immunogenicity of *V. cholerae* O139 Capsular Polysaccharide Conjugates with Recombinant Diphtheria Toxin Mutant in Mice. Infect Immun. 2000; 68(9): 5037-5043.*

Martin, et al. A simple vector system to improve performance and utilisation of recombinant antibodies. BMC Biotechnology. 2006; 6(46): 1-15.*

De Filette et al., "The universal influenza vaccine M2e—HBc administered intranasally in combination with the adjuvant CTA1-DD provides complete protection," J.Vaccine, No. 5613 8 pp. (2005).

Fan et al., "Preclinical study of influenza virus A M2 peptide conjugate vaccines in mice, ferrets, and rhesus monkeys," J.Vaccine, 22, p. 2993-3003 (2004).

Kubler-Kielb et al., "Additional Conjugation Methods and Immuogenicity of *Bacillus anhtracis* Poly-γ-D-Glutamic Acid-Protein Conjugates,"Infection and Immunity, 74:8, pp. 4744-4749 (Aug. 2006).

Robbins et al., "Synthesis, characterization, and immunogenicity in mice of *Shigella sonnei* O-specific oligosaccharide-core-protein conjugates," PNAS, 106:19, pp. 7974-7978 (May 12, 2009).

Robbins et al., "Development of Vaccines Against Bacterial Diseases, Especially in Children," Annual Report of the Division of Intermural Research (Apr. 30, 2008).

Song et al., "Efficacious Recombinant Influenza Vaccines Produced by High Yield Bacterial Expression: A Solution to Global Pandemic and Seasonal Needs," PLOS One 3:5, 8pp. (May 2008).

Taylor et al., "Synthesis, Characterization, and Clinical Evaluation of Conjugate Vaccines Composed of the O-Specific Polysaccharides of *Shigella dysenteriae* Type 1, *Shigella flexneri* Type 2a, and *Shigella sonnei* (*Plesiomonas shigelloides*) Bound to Bacterial Toxoids," Infection and Immunity, 61(9):3678-3687 (Sep. 1993).

Tompkins et al., "Matrix Protein 2 Vaccination and Protection against Influenza Viruses, Including Subtype H5N1," Emerging Infectious Diseases, 13(3):426-435 (Mar. 2007).

* cited by examiner

FIG. 5

SEQUENCE LISTING

```
<160> NUMBER OF SEQ ID NOS: 6

<210> SEQ ID NO 1
<211> LENGTH: 84
<212> TYPE: DNA
<213> ORGANISM: Artificial Sequence
<220> FEATURE:
<223> OTHER INFORMATION: Synthetic Oligonucleotide Primer

<400> SEQUENCE: 1
aaggaaaaaa gcggccgctc attaatggtg atgatgatgg tggccaccgc cttggtaaat        60
tccaattgat tccaatttta ctcc                                               84

<210> SEQ ID NO 2
<211> LENGTH: 82
<212> TYPE: DNA
<213> ORGANISM: Artificial Sequence
<220> FEATURE:
<223> OTHER INFORMATION: Synthetic Oligonucleotide Primer

<400> SEQUENCE: 2
catgccatgg gtgatcagat ttgcattggt taccatgcaa acaactcgac agagcaggtc        60
gacacaatta tggaaaagaa cg                                                 82

<210> SEQ ID NO 3
<211> LENGTH: 24
<212> TYPE: PRT
<213> ORGANISM: Artificial Sequence
<220> FEATURE:
<223> OTHER INFORMATION: Influenza Matrix Protein 2 ectodomain consensus
      sequence.
<220> FEATURE:
<221> NAME/KEY: MISC_FEATURE
<222> LOCATION: (1)..(1)
<223> OTHER INFORMATION: Xaa can be serine or valine
<220> FEATURE:
<221> NAME/KEY: MISC_FEATURE
<222> LOCATION: (9)..(9)
<223> OTHER INFORMATION: Xaa can be proline, leucine or histidine
<220> FEATURE:
<221> NAME/KEY: MISC_FEATURE
<222> LOCATION: (10)..(10)
<223> OTHER INFORMATION: Xaa can be isoleucine or threonine
<220> FEATURE:
```

```
<221> NAME/KEY: MISC_FEATURE
<222> LOCATION: (11)..(11)
<223> OTHER INFORMATION: Xaa can be arginine or lysine
<220> FEATURE:
<221> NAME/KEY: MISC_FEATURE
<222> LOCATION: (12)..(12)
<223> OTHER INFORMATION: Xaa can be asparigine or serine
<220> FEATURE:
<221> NAME/KEY: MISC_FEATURE
<222> LOCATION: (13)..(13)
<223> OTHER INFORMATION: Xaa can be glutamic acid or glycine
<220> FEATURE:
<221> NAME/KEY: MISC_FEATURE
<222> LOCATION: (15)..(15)
<223> OTHER INFORMATION: Xaa can be glycine or glutamic acid
<220> FEATURE:
<221> NAME/KEY: MISC_FEATURE
<222> LOCATION: (17)..(17)
<223> OTHER INFORMATION: Xaa can be arginine or lysine
<220> FEATURE:
<221> NAME/KEY: MISC_FEATURE
<222> LOCATION: (18)..(18)
<223> OTHER INFORMATION: Xaa can be cysteine or tyrosine
<220> FEATURE:
<221> NAME/KEY: MISC_FEATURE
<222> LOCATION: (19)..(19)
<223> OTHER INFORMATION: Xaa can be glutamine or serine
<220> FEATURE:
<221> NAME/KEY: MISC_FEATURE
<222> LOCATION: (20)..(20)
<223> OTHER INFORMATION: Xaa can be aspartic acid or glycine
<220> FEATURE:
<221> NAME/KEY: MISC_FEATURE
<222> LOCATION: (21)..(21)
<223> OTHER INFORMATION: Xaa can be serine or leucine
<220> FEATURE:
<221> NAME/KEY: MISC_FEATURE
<222> LOCATION: (22)..(22)
<223> OTHER INFORMATION: Xaa can be serine or arginine
<220> FEATURE:
<221> NAME/KEY: MISC_FEATURE
<222> LOCATION: (23)..(23)
<223> OTHER INFORMATION: Xaa can be aspartic acid or glutamic acid

<400> SEQUENCE: 3

Xaa Leu Leu Thr Glu Val Glu Thr Xaa Xaa Xaa Xaa Xaa Trp Xaa Cys
1               5                   10                  15

Xaa Xaa Xaa Xaa Xaa Xaa Xaa Cys
            20

<210> SEQ ID NO 4
<211> LENGTH: 24
<212> TYPE: PRT
<213> ORGANISM: Artificial Sequence
<220> FEATURE:
<223> OTHER INFORMATION: Exemplary M2e peptide.

<400> SEQUENCE: 4

Ser Leu Leu Thr Glu Val Glu Thr Pro Thr Arg Asn Glu Trp Glu Cys
1               5                   10                  15

Arg Cys Ser Asp Ser Ser Asp Cys
            20

<210> SEQ ID NO 5
<211> LENGTH: 23
<212> TYPE: PRT
<213> ORGANISM: Influenza A virus

<400> SEQUENCE: 5

Ser Leu Leu Thr Glu Val Glu Thr Pro Ile Arg Asn Glu Trp Gly Cys
1               5                   10                  15

Arg Cys Asn Asp Ser Ser Asp
```

<210> SEQ ID NO 6
<211> LENGTH: 526
<212> TYPE: PRT
<213> ORGANISM: Artificial Sequence
<220> FEATURE:
<223> OTHER INFORMATION: Recombinant Influenza HA Immunogen.

<400> SEQUENCE: 6

```
Met Gly Asp Gln Ile Cys Ile Gly Tyr His Ala Asn Asn Ser Thr Glu
1               5                   10                  15

Gln Val Asp Thr Ile Met Glu Lys Asn Val Thr Val Thr His Ala Gln
            20                  25                  30

Asp Ile Leu Glu Lys Lys His Asn Gly Lys Leu Cys Asp Leu Asp Gly
        35                  40                  45

Val Lys Pro Leu Ile Leu Arg Asp Cys Ser Val Ala Gly Trp Leu Leu
    50                  55                  60

Gly Asn Pro Met Cys Asp Glu Phe Ile Asn Val Pro Glu Trp Ser Tyr
65                  70                  75                  80

Ile Val Glu Lys Ala Asn Pro Val Asn Asp Leu Cys Tyr Pro Gly Asp
                85                  90                  95

Phe Asn Asp Tyr Glu Glu Leu Lys His Leu Leu Ser Arg Ile Asn His
            100                 105                 110

Phe Glu Lys Ile Gln Ile Ile Pro Lys Ser Ser Trp Ser Ser His Glu
        115                 120                 125

Ala Ser Leu Gly Val Ser Ser Ala Cys Pro Tyr Gln Gly Lys Ser Ser
    130                 135                 140

Phe Phe Arg Asn Val Val Trp Leu Ile Lys Lys Asn Ser Thr Tyr Pro
145                 150                 155                 160

Thr Ile Lys Arg Ser Tyr Asn Asn Thr Asn Gln Glu Asp Leu Leu Val
                165                 170                 175

Leu Trp Gly Ile His His Pro Asn Asp Ala Ala Glu Gln Thr Lys Leu
            180                 185                 190

Tyr Gln Asn Pro Thr Thr Tyr Ile Ser Val Gly Thr Ser Thr Leu Asn
        195                 200                 205

Gln Arg Leu Val Pro Arg Ile Ala Thr Arg Ser Lys Val Asn Gly Gln
    210                 215                 220

Ser Gly Arg Met Glu Phe Phe Trp Thr Ile Leu Lys Pro Asn Asp Ala
225                 230                 235                 240

Ile Asn Phe Glu Ser Asn Gly Asn Phe Ile Ala Pro Glu Tyr Ala Tyr
                245                 250                 255

Lys Ile Val Lys Lys Gly Asp Ser Thr Ile Met Lys Ser Glu Leu Glu
            260                 265                 270

Tyr Gly Asn Cys Asn Thr Lys Cys Gln Thr Pro Met Gly Ala Ile Asn
        275                 280                 285

Ser Ser Met Pro Phe His Asn Ile His Pro Leu Thr Ile Gly Glu Cys
    290                 295                 300

Pro Lys Tyr Val Lys Ser Asn Arg Leu Val Leu Ala Thr Gly Leu Arg
305                 310                 315                 320

Asn Ser Pro Gln Arg Glu Arg Arg Lys Arg Gly Leu Phe Gly
                325                 330                 335

Ala Ile Ala Gly Phe Ile Glu Gly Gly Trp Gln Gly Met Val Asp Gly
            340                 345                 350

Trp Tyr Gly Tyr His His Ser Asn Glu Gln Gly Ser Gly Tyr Ala Ala
        355                 360                 365
```

```
Asp Lys Glu Ser Thr Gln Lys Ala Ile Asp Gly Val Thr Asn Lys Val
    370                 375                 380

Asn Ser Ile Ile Asp Lys Met Asn Thr Gln Phe Glu Ala Val Gly Arg
385                 390                 395                 400

Glu Phe Asn Asn Leu Glu Arg Arg Ile Glu Asn Leu Asn Lys Lys Met
                405                 410                 415

Glu Asp Gly Phe Leu Asp Val Trp Thr Tyr Asn Ala Glu Leu Leu Val
                420                 425                 430

Leu Met Glu Asn Glu Arg Thr Leu Asp Phe His Asp Ser Asn Val Lys
        435                 440                 445

Asn Leu Tyr Asp Lys Val Arg Leu Gln Leu Arg Asp Asn Ala Lys Glu
    450                 455                 460

Leu Gly Asn Gly Cys Phe Glu Phe Tyr His Lys Cys Asp Asn Glu Cys
465                 470                 475                 480

Met Glu Ser Val Arg Asn Gly Thr Tyr Asp Tyr Pro Gln Tyr Ser Glu
                485                 490                 495

Glu Ala Arg Leu Lys Arg Glu Glu Ile Ser Gly Val Lys Leu Glu Ser
            500                 505                 510

Ile Gly Ile Tyr Gln Gly Gly Gly His His His His His His
        515                 520                 525
```

VACCINES AGAINST INFLUENZA VIRUS

CROSS REFERENCE TO RELATED APPLICATION

This application claims the benefit of U.S. Provisional Application No. 61/089,384, filed Aug. 15, 2008, which is incorporated herein by reference in its entirety.

FIELD

Disclosed herein are immunogens and immunogenic composition for influenza virus produced from influenza derived peptides, methods of producing such vaccines and methods of treating subjects with such vaccines.

BACKGROUND

Influenza virus types A and B are members of the orthomyxoviridae family of viruses that cause influenza infection. Influenza A and B viruses primarily infect the nasopharyngeal and oropharyngeal cavities and produce highly contagious, acute respiratory disease that can result in significant morbidity and high economic costs. Typical influenza viral infections in humans have a relatively short incubation period of 1 to 2 days, with symptoms that last about a week including an abrupt onset of fever, sore throat, cough, headache, myalgia, and malaise. When a subject is infected with a highly virulent strain of influenza these symptoms can progress rapidly to pneumonia and in some circumstances death. Pandemic outbreaks of highly virulent influenza present a serious risk to human and animal health worldwide.

Genetic reassortment between human and avian influenza viruses can result in a virus with a novel hemagglutinin (HA) of avian origin, against which humans lack immunity. Recombination between avian strains and human strains in coinfected individuals has given rise to recombinant influenza viruses to which immunity is lacking in the human population, resulting in influenza pandemics. In the $20^{th}$ century, the pandemics of 1918, 1957 and 1968 were the result of such antigenic shifts.

Highly pathogenic avian influenza H5N1 viruses have become endemic in domestic poultry in Southeast Asia. Since early 2004, human infections with H5N1 viruses have been reported in the region with increasing frequency and high mortality rates. Highly pathogenic H5N1 influenza viruses were first recognized to cause respiratory disease in humans in 1997, when 18 documented cases, including 6 deaths, occurred following outbreaks of influenza in poultry farms and markets in Hong Kong. Two additional human H5N1 infections were identified in a family in Hong Kong in 2003. Since then, H5N1 viruses have spread to many Asian countries, as well as countries in Eastern Europe. The laboratory confirmed cases of human infection since January 2004 have had a fatality rate of greater than 50% as reported to the World Health Organization. To date, most of the human H5N1 virus infections have been due to direct transmission of the virus from infected poultry, although exceptional cases of human-to-human transmission have been reported.

The recent outbreaks of avian influenza caused by H5N1, H7N7 and H9N2 subtype influenza viruses, and their infection of humans have created a new awareness of the pandemic potential of influenza viruses that circulate in domestic poultry. The estimated economic impact of a pandemic would be up to $165 billion in the United States alone, with as many as 200,000 deaths, 730,000 hospitalizations, 42 outpatient visits, and 50 million additional illnesses.

Due to the lethality of these influenza strains in poultry, current vaccine production strategies involving growth of virus in hen's eggs are not feasible. Some approaches have focused on isolating non-pathogenic or attenuated strains of influenza that express the relevant immunogenic antigens of the potentially pandemic influenza strains. For example, naturally occurring, apathogenic strains of influenza with the H5 subtype antigen virus have been evaluated as vaccine candidates. In general, these viruses have proved difficult to grow using conventional technology, and protection is dependent on the ability of antibodies raised against the apathogenic vaccine strain to cross-react with the virulent strain of virus (Takada et al., *J. Virol.* 73:8303-8307, 1999; Wood et al., *Vaccine* 18:579-80, 2000).

A reverse genetics approach has been employed to delete a stretch of basic amino acids at the cleavage site of the HA antigen of a pathogenic H5N1 virus (A/HK/97) to develop a candidate vaccine (Li et al., *J. Infect. Dis.* 179:1132-1138, 1999).

Another approach has been to utilize recombinant HA ("H5") produced in a baculovirus expression system. However, high doses of purified protein and the use of adjuvants are required to achieve a satisfactory immune response. (Treanor et al. *Vaccine* 19:1732-1737, 2001). Furthermore the production of protein from a baculovirus expression system in insect cells is laborious and time consuming.

Thus, there remains a need to develop vaccines that are protective against infection by influenza strains in both human and non-human populations, which can be efficiently produced and administered without reliance on viral growth in hen's eggs.

SUMMARY

The present disclosure provides novel compositions and methods for producing influenza vaccines and vaccinating humans, non-human mammals and avian populations against avian and/or pandemic strains of influenza virus and overcoming the poor immunogenicity and manufacturing drawbacks of currently available influenza vaccines, which have been adapted to elicit an immune response against avian strains of influenza.

Some of the conjugates are immunogenic conjugates that include an influenza M2 ectodomain (M2e) peptide covalently linked to a carrier by a thioether linkage between a lysine amino acid residue present in carrier and a cysteine amino acid residue introduced at the C-terminal end of the M2e peptide. The conjugated have the general formula:

$$\text{M2e-Cys-S}-CH_2-C(O)-NH-CH_2-CH_2-C(O-)NH-Lys-Pr,$$

where M2e is the influenza M2 ectodomain (M2e) peptide; Cys is a cysteine amino acid residue present in the M2e peptide; S the sulfur present in the cysteine amino acid residue; CH2-CO—NH—CH2-CH2-CO the linking group; NH the amine group present in a lysine residue of the carrier; Lys is a lysine amino acid residue and Pr the carrier protein.

In some examples the carrier is bovine serum albumin, recombinant *B. anthracis* protective antigen, recombinant *P. aeruginosa* exotoxin A, tetanus toxoid, recombinant diphtheria toxoid, pertussis toxoid, *C. perfringens* toxoid, keyhole limpet hemocyanin, horseshoe crab hemocyanin, edestin, mammalian serum albumins, mammalian immunoglobulins, or analogs or mimetics of and combinations of two or more thereof. In specific examples, the carrier is detoxified recombinant diphtheria toxin (rDT), such as rDT-H21G. This M2e peptide used in the disclosed immunogenic conjugates include the an amino acid sequence set forth as $X_1LLTEVETX_2X_3X_4X_5X_6WX_7CX_8X_9X_{10}X_{11}X_{12}X_{13}X_{14}C$ (SEQ ID NO: 3), where $X_1$ can be serine or valine; $X_2$ can be proline, leucine or histidine; $X_3$ can be isoleucine or threonine; $X_4$ can be arginine or lysine; $X_5$ can be asparigine or serine; $X_6$ can be glutamic acid or glycine; $X_7$ can be glycine or glutamic acid; $X_8$ can be arginine or lysine; $X_9$ can be cysteine or tyrosine; $X_{10}$ can be glutamine or serine; $X_{11}$ can be aspartic acid or glycine; $X_{12}$ can be serine or leucine; $X_{13}$ can be serine or arginine; and $X_{14}$ can be aspartic acid or glutamic acid. In specific examples the M2e peptide includes the amino acid sequence set forth as SLLTEVETPTRNEWECRCSDSSDC (SEQ ID NO: 4).

Also disclosed are isolated immunogens that include an immunogenic fragment of an influenza HA protein including the polybasic cleavage site, wherein the immunogenic fragment of the influenza HA protein has been modified to remove an N-terminal leader amino acid sequence and a C-terminal transmembrane domain. In some examples, the immunogenic fragment of the influenza HA protein is not glycosylated. In some examples, the immunogenic fragment of an influenza HA protein includes a six residue histidine tag linked by a peptide linker to the C-terminal end of the immunogenic fragment of the influenza HA protein. In some examples, the immunogen includes an adjuvant, such as alum, to which the immunogenic fragment of the influenza HA protein is adsorbed.

Disclosed are methods producing an influenza vaccine specific for an identified influenza strain. The methods include obtaining a nucleic acid sequence of the identified influenza strain encoding a hemagglutinin (HA) from the identified influenza strain and producing a nucleic acid molecule encoding an immunogenic fragment of the HA, wherein the nucleic acid molecule encodes the polybasic cleavage site, and wherein the nucleic acid molecule does not encode a leader sequence at the N-terminal end of the HA or a transmembrane domain at the C-terminal end of immunogenic fragment of the HA. The immunogenic fragment of the HA is expressed from the nucleic acid molecule in a bacterial expression system, thereby producing an influenza vaccine specific for an identified influenza strain.

The immunogenic conjugates and immunogens disclosed herein are useful in the context of immunogenic compositions, including vaccines.

The present disclosure also provides methods for eliciting or producing an immune response against influenza. The methods disclosed herein involve administering one or more of the disclosed immunogenic conjugates, immunogens and/or immunogenic compositions to a subject. Administration of the immunogenic conjugates, immunogens and/or immunogenic compositions can elicit an immune response that protects the subject from serious disease or death due to infection by influenza. Typically, the immune response includes neutralizing antibodies that bind to at least one avian influenza antigen.

The foregoing and other objects, features, and advantages of the invention will become more apparent from the following detailed description, which proceeds with reference to the accompanying figures.

BRIEF DESCRIPTION OF THE DRAWINGS

FIG. 5 is referred to as Table 3 in the text and includes the conserved human sequence of the M2e peptide (SEQ ID NO: 5).

BRIEF DESCRIPTION OF THE SEQUENCE LISTING

Figure 1:
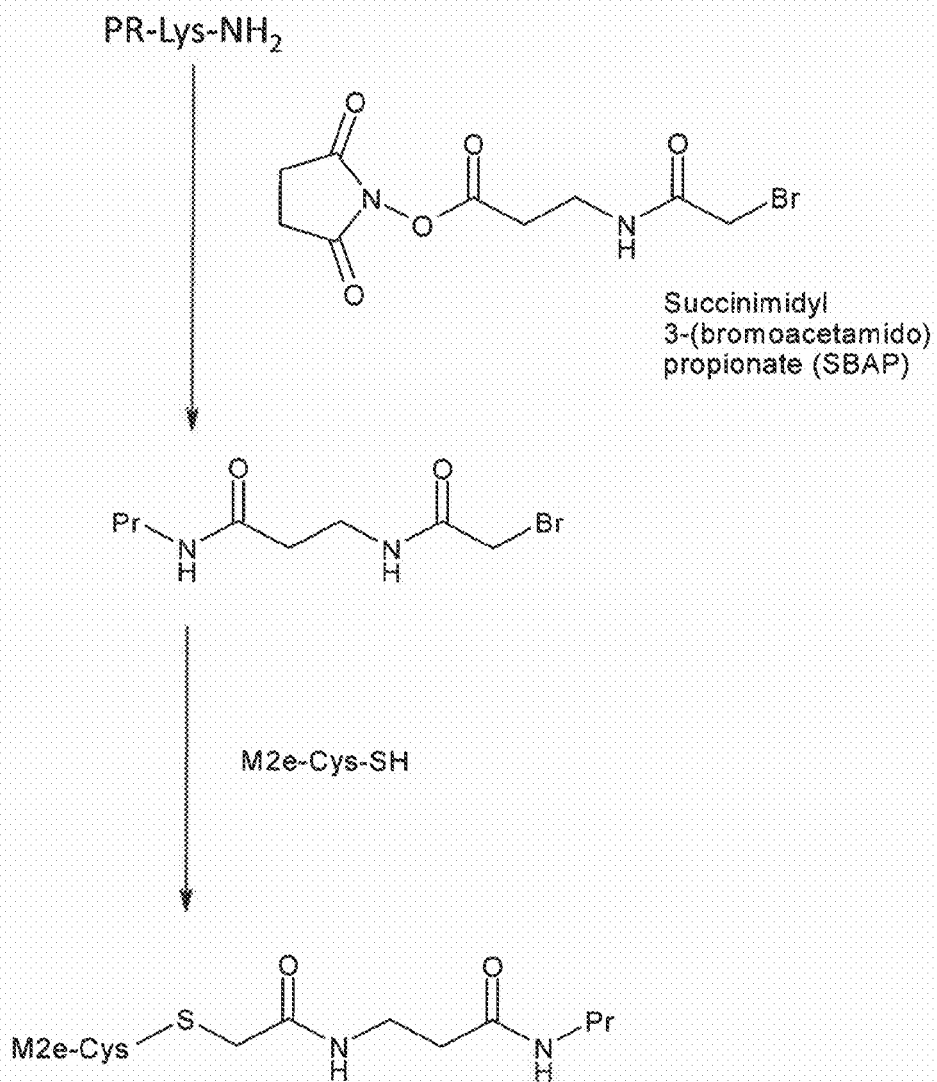
FIG. 1 is a schematic representation of the conjugation of M2e peptide to carrier protein via a thioether linkage.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

SEQ ID NOs: 1 and 2 are nucleic acid sequences of exemplary synthetic oligonucleotide primers for the amplification of HA.

SEQ ID NO: 3 is the amino acid sequence of a consensus sequence of the M2e peptide.

SEQ ID NO: 4 is the amino acid sequence of an exemplary M2e peptide.

SEQ ID NO: 5 is the amino acid sequence of conserved human sequence of the M2e peptide.

SEQ ID NO: 6 is the amino acid sequence of an exemplary HA immunogen.

DETAILED DESCRIPTION

I. Listing of Terms

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references. In case of conflict, the present specification, including explanations of terms, will control.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all nucleotide sizes or amino acid sizes, and all molecular weight or molecular mass values, given for nucleic acids or polypeptides or other compounds are approximate, and are provided for description.

Although methods and materials similar or equivalent to those described herein can be used in the practice or testing of the present disclosure, suitable methods and materials are described below. In addition, the materials, methods, and examples are illustrative only and not intended to be limiting.

To facilitate review of the various examples of this disclosure, the following explanations of specific terms are provided:

Adjuvant: A substance that non-specifically enhances the immune response to an antigen. Development of vaccine adjuvants for use in humans is reviewed in Singh et al. (*Nat. Biotechnol.* 17:1075-1081, 1999), which discloses that, at the time of its publication, aluminum salts, such as aluminum hydroxide (AMPHOGEL®, Wyeth Laboratories, Madison, N.J.), and the MF59 microemulsion are the only vaccine adjuvants approved for human use. An aluminum hydrogel (available from Brentg Biosector, Copenhagen, Denmark is another common adjuvant).

In one embodiment, an adjuvant includes a DNA motif that stimulates immune activation, for example the innate immune response or the adaptive immune response by T-cells, B-cells, monocytes, dendritic cells, and natural killer cells. Specific, non-limiting examples of a DNA motif that stimulates immune activation include CpG oligodeoxynucleotides, as described in U.S. Pat. Nos. 6,194,388; 6,207,646; 6,214,806; 6,218,371; 6,239,116; 6,339,068; 6,406,705; and 6,429,199.

Administration: The introduction of a composition into a subject by a chosen route. For example, if the chosen route is intravenous, the composition is administered by introducing the composition into a vein of the subject. All methods of administration are contemplated by this disclosure.

Amplification: To increase the number of copies of a nucleic acid molecule. The resulting amplification products are called "amplicons." Amplification of a nucleic acid molecule (such as a DNA or RNA molecule) refers to use of a technique that increases the number of copies of a nucleic acid molecule in a sample, for example the number of copies of an influenza HA nucleic acid. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include quantitative real-time PCR; reverse transcriptase PCR (RT-PCR); real-time PCR (rt PCR); real-time reverse transcriptase PCR (rt RT-PCR); nested PCR; strand displacement amplification (see U.S. Pat. No. 5,744,311); transcription-free isothermal amplification (see U.S. Pat. No. 6,033,881, repair chain reaction amplification (see WO 90/01069); ligase chain reaction amplification (see European patent publication EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134) amongst others.

Analog, Derivative or Mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19th Edition (1995), chapter 28). A derivative is a biologically active molecule derived from the base structure. A mimetic is a molecule that mimics the activity of another molecule, such as a biologically active molecule. Biologically active molecules can include chemical structures that mimic the biological activities of a compound.

Animal: Living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

Antigen: A compound, composition, or substance that can stimulate the production of antibodies or a T cell response in an animal, including compositions that are injected, absorbed or otherwise introduced into an animal. The term "antigen" includes all related antigenic epitopes. An "antigenic polypeptide" is a polypeptide to which an immune response, such as a T cell response or an antibody response, can be stimulated. "Epitope" or "antigenic determinant" refers to a site on an antigen to which B and/or T cells respond. In one embodiment, T cells respond to the epitope when the epitope is presented in conjunction with an MHC molecule. Epitopes can be formed both from contiguous amino acids or noncontiguous amino acids juxtaposed by tertiary folding of an antigenic polypeptide. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and multi-dimensional nuclear magnetic resonance spectroscopy.

An influenza antigen can be a hemagglutinin (HA) or a portion or fragment thereof. An influenza antigen can also be an influenza internal protein, such as a M2 protein of fragment thereof, for example the M2 ectodomain (M2e).

cDNA (complementary DNA): A piece of DNA lacking internal, non-coding segments (introns) and regulatory sequences that determine transcription. cDNA is typically synthesized in the laboratory by reverse transcription from RNA, such as messenger RNA extracted from cells and/or viral RNA, for exam RNA encoding an influenza HA polypeptide. In the context of preparing immunogen, immunogenic conjugates and vaccines of the present disclosure, for example from a polynucleotide sequences that encode influenza antigen (such as HA or M2e), a cDNA can be prepared, for example by reverse transcription or amplification (e.g., by the polymerase chain reaction, PCR) from a negative stranded influenza RNA genome (or genome segment).

Carrier: An immunogenic molecule to which a hapten or an antigen such as an influenza antigen (for example HA or a portion thereof or M2e), can be bound. When bound to a carrier, the bound molecule may become more immunogenic. Carriers are chosen to increase the immunogenicity of the bound molecule and/or to elicit antibodies against the carrier which are diagnostically, analytically, and/or therapeutically beneficial. Covalent linking of a molecule to a carrier confers enhanced immunogenicity and T-cell dependence (Pozsgay et al., *PNAS* 96:5194-97, 1999; Lee et al., *J. Immunol.* 116: 1711-18, 1976; Dintzis et al., *PNAS* 73:3671-75, 1976). Useful carriers include polymeric carriers, which can be natural (for example, proteins from bacteria or viruses), semi-synthetic or synthetic materials containing one or more functional groups to which a reactant moiety can be attached.

Examples of bacterial products for use as carriers include bacterial toxins, such as recombinant diphtheria toxin (including fragments that contain at least one antigenic epitope and analogs or derivatives capable of eliciting an immune response), LF and LeTx, and other bacterial toxins and toxoids, such as tetanus toxin/toxoid, *P. aeruginosa* exotoxin/toxoid/, pertussis toxin/toxoid, and *C. perfringens* exotoxin/toxoid. Viral proteins, such as hepatitis B surface antigen and core antigen can also be used as carriers.

Codon optimization: The process of altering the nucleic acid sequence encoding a polypeptide (such as an influenza polypeptide, for example and influenza HA or M2e polypeptide) to increase the expression of the peptide in a particular host cell (such as *Escherichia coli* (*E. coli*)) with out altering the amino acid sequence of the polypeptide.

Because there are four nucleotides in DNA, adenine (A), guanine (G), cytosine (C) and thymine (T), there are 64 possible triplets encoding 20 amino acids, and three translation termination (nonsense) codons. Because of this redundancy, all but two amino acids are encoded by more than one triplet. Different organisms often show particular preferences for one of the several codons that encode the same amino acid. Optimal codons in fast-growing microorganisms, like *E. coli*, are believed to reflect the composition of their respective genomic tRNA pool. Thus, by altering the codons present in a particular nucleic acid that expresses a polypeptide, through codon optimization, the expression level, that is the amount of the polypeptide expressed, can be increased.

Complementary: A double-stranded DNA or RNA strand consists of two complementary strands of base pairs. Complementary binding occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'.

Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions.

Degenerate variant and conservative variant: A polynucleotide encoding a polypeptide or an antibody that includes a sequence that is degenerate as a result of the genetic code. For example, a polynucleotide encoding an immunogenic fragment of an influenza HA polypeptide, includes a sequence that is degenerate as a result of the genetic code. There are 20 natural amino acids, most of which are specified by more than one codon. Therefore, all degenerate nucleotide sequences are included as long as the amino acid sequence of the immunogenic fragment of an influenza HA polypeptide encoded by the nucleotide sequence is unchanged. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified within a protein encoding sequence, the codon can be altered to any of the corresponding codons described without altering the encoded protein, for example in the process of codon optimization. Such nucleic acid variations are "silent variations," which are one species of conservative variations. Each nucleic acid sequence herein that encodes a polypeptide also describes every possible silent variation. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence.

Furthermore, one of ordinary skill will recognize that individual substitutions, deletions or additions which alter, add or delete a single amino acid or a small percentage of amino acids (for instance less than 5%, such as less than 4%, less than 3%, less than 2%, or even less than 1%) in an encoded sequence are conservative variations where the alterations result in the substitution of an amino acid with a chemically similar amino acid.

Conservative amino acid substitutions providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Not all residue positions within a protein will tolerate an otherwise "conservative" substitution. For instance, if an amino acid residue is essential for a function of the protein, even an otherwise conservative substitution may disrupt that activity.

Covalent Bond: An interatomic bond between two atoms, characterized by the sharing of one or more pairs of electrons by the atoms. The terms "covalently bound" or "covalently linked" refer to making two separate molecules into one contiguous molecule. The terms include reference to joining a hapten or antigen (such as an influenza antigen) indirectly to a carrier molecule, with an intervening linker molecule, such as a peptide linker.

Epitope or Antigenic Epitope: An antigenic determinant. These are particular chemical groups or contiguous or non-contiguous peptide sequences on a molecule that are antigenic, that is, that elicit a specific immune response. An antibody binds a particular antigenic epitope based on the three dimensional structure of the antibody and the matching (or cognate) epitope.

Expression: Translation of a nucleic acid into a protein, for example the translation of a nucleic acid molecule encoding an immunogenic fragment of an influenza HA polypeptide into a protein.

Expression Control Sequences: Nucleic acid sequences that regulate the expression of a heterologous nucleic acid sequence to which it is operatively linked, for example the expression of nucleic acid encoding an immunogenic fragment of an influenza HA polypeptide operably linked to expression control sequences. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence, which facilitates the efficient transcription of the inserted genetic sequence of the host. The expression vector typically contains an origin of replication, a promoter, as well as specific nucleic acid sequences that allow phenotypic selection of the transformed cells.

Fixative: A reagent with at least one chemical group that is reactive to a functional group present in proteins, such as sulfhydryls and/or amine groups. In some examples, a fixative is amine reactive, meaning it is capable of forming a covalent bond with an amine group, such as an amine group present in a protein, for example an amine group present on a lysine or arginine residue. Examples of fixative that are amine reactive are aldehydes such as formaldehyde, paraformaldehyde, glyoxal, glutaraldehyde, adipaldehyde, succinaldehyde, and suberaldehyde. In some examples a fixative is formaldehyde in the form of a formalin solution (which is typically about 4% formaldehyde in a buffer solution, referred to as 10% buffered formalin).

Host cells: Cells in which a polynucleotide, for example, a polynucleotide vector, can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used. Thus, vectors encoding the peptides of the vaccines described herein can be introduced into host cells where their polynucleotide sequences (including those encoding influenza antigen(s)) can be expressed, for example to produce recombinant influenza antigens and/or carriers.

Hybridization: The ability of complementary single-stranded DNA or RNA to form a duplex molecule (also referred to as a hybridization complex). Nucleic acid hybridization techniques can be used to form hybridization complexes between a probe or primer and a nucleic acid, such as an influenza nucleic acid. For example, a probe or primer having some homology to an influenza nucleic acid molecule will form a hybridization complex with an influenza nucleic acid molecule. Hybridization occurs between a single stranded probe and a single stranded target nucleic acid (such as an influenza nucleic acid). When the target nucleic acid is initially one strand of a duplex nucleic acid the duplex must be melted (at least partially) for the probe to hybridize.

Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (Detects Sequences that Share at Least 90% Identity)
  Hybridization: 5×SSC at 65° C. for 16 hours
  Wash twice: 2×SSC at room temperature (RT) for 15 minutes each
  Wash twice: 0.5×SSC at 65° C. for 20 minutes each
High Stringency (Detects Sequences that Share at Least 80% Identity)
  Hybridization: 5×-6×SSC at 65° C.-70° C. for 16-20 hours
  Wash twice: 2×SSC at RT for 5-20 minutes each
  Wash twice: 1×SSC at 55° C.-70° C. for 30 minutes each
Low Stringency (Detects Sequences that Share at Least 50% Identity)
  Hybridization: 6×SSC at RT to 55° C. for 16-20 hours
  Wash at least twice: 2×-3×SSC at RT to 55° C. for 20-30 minutes each.

Influenza Virus: Influenza viruses are enveloped negative-sense viruses belonging to the orthomyxoviridae family. Influenza viruses are classified on the basis of their core proteins into three distinct types: A, B, and C. Within these broad classifications, subtypes are further divided based on the characterization of two antigenic surface proteins hemagglutinin (HA or H) and neuraminidase (NA or N). While B and C type influenza viruses are largely restricted to humans, influenza A viruses are pathogens of a wide variety of species including humans, non-human mammals, and birds. Periodically, non-human strains, particularly of avian influenza, have infected human populations, in some cases causing severe disease with high mortality. Recombination between such avian strains and human strains in coinfected individuals has given rise to recombinant influenza viruses to which immunity is lacking in the human population, resulting in influenza pandemics. Three such pandemics occurred during the twentieth century (pandemics of 1918, 1957, and 1968) and resulted in numerous deaths world-wide.

Influenza viruses have a segmented single-stranded (negative or antisense) genome. The influenza virion consists of an internal ribonucleoprotein core containing the single-stranded RNA genome and an outer lipoprotein envelope lined by a matrix protein. The segmented genome of influenza consists of eight linear RNA molecules that encode ten polypeptides. Two of the polypeptides, HA and NA include the primary antigenic determinants or epitopes required for a protective immune response against influenza. Based on the antigenic characteristics of the HA and NA proteins, influenza strains are classified into subtypes. For example, recent outbreaks of avian influenza in Asia have been categorized as H5N1, H7N7, and H9N2 based on their HA and NA phenotypes.

HA is a surface glycoprotein which projects from the lipoprotein envelope and mediates attachment to and entry into cells. The HA protein is approximately 566 amino acids in length, and is encoded by an approximately 1780 base polynucleotide sequence of segment 4 of the genome. Polynucleotide and amino acid sequences of HA (and other influenza antigens) isolated from recent, as well as historic, avian influenza strains can be found, for example in the GENBANK® database (available on the world wide web at ncbi.nlm.nih.gov/entrez) or the Influenza Sequence Database of Los Alamos National Laboratories (LANL) (available on the world wide web at flu.lanl.gov). For example, recent avian H1 subtype HA sequences include: AY038014, and J02144; recent avian H3 subtype HA sequences include: AY531037, M29257, and U97740; H5 subtype HA sequences include: AY075033, AY075030, AY818135, AF046097, AF046096, and AF046088; recent H7 subtype HA sequences include: AJ704813, AJ704812, and Z47199; and, recent avian H9 subtype HA sequences include: AY862606, AY743216, and AY664675.

The mature influenza HA polypeptide includes a polybasic cleavage site, and a C-terminal transmembrane domain. The N-terminal leader amino acid sequence is cleaved during processing.

In addition to the HA antigen, which is the predominant target of neutralizing antibodies against influenza, the neuraminidase (NA) envelope glycoprotein is also a target of the protective immune response against influenza. NA is an approximately 450 amino acid protein encoded by an approximately 1410 nucleotide sequence of influenza genome segment 6. Recent pathogenic avian strains of influenza have belonged to the N1, N7 and N2 subtypes. Exemplary NA polynucleotide and amino acid sequences include for example, N1: AY651442, AY651447, and AY651483; N7: AY340077, AY340078 and AY340079; and, N2: AY664713, AF508892, and AF508588.

The remaining segments of the influenza genome encode the internal proteins. PB2 is a 759 amino acid polypeptide which is one of the three proteins which comprise the RNA-dependent RNA polymerase complex. PB2 is encoded by approximately 2340 nucleotides of the influenza genome segment 1. The remaining two polymerase proteins, PB1, a 757 amino acid polypeptide, and PA, a 716 amino acid polypeptide, are encoded by a 2341 nucleotide sequence and a 2233 nucleotide sequence (segments 2 and 3), respectively.

Segment 5 consists of about 1565 nucleotides encoding an about 498 amino acid nucleoprotein (NP) protein that forms the nucleocapsid.

Segment 7 consists of an about 1027 nucleotide sequence of the M gene, which encodes the two matrix proteins; an about 252 amino acid M1 protein, and an about 96 amino acid M2 protein, which is translated from a spliced variant of the M RNA. The M2 protein includes a C-terminal portion termed the influenza M2 ectodomain (M2e).

Segment 8 consists of the NS gene, which encodes two different non-structural proteins, NS1 and NS2.

Immune response: A response of a cell of the immune system, such as a B cell, T cell, or monocyte, to a stimulus. In some cases, the response is specific for a particular antigen (that is, an "antigen-specific response"). In some cases, an immune response is a T cell response, such as a CD4+ response or a CD8+ response. Alternatively, the response is a B cell response, and results in the production of specific antibodies. A "protective immune response" is an immune response that inhibits a detrimental function or activity of an influenza virus, reduces infection by a pathogenic influenza virus, or decreases symptoms (including death) that result from infection by the pathogenic organism. A protective immune response can be measured, for example, by the inhibition of viral replication or plaque formation in a plaque reduction assay or ELISA-neutralization assay (NELISA), or by measuring resistance to viral challenge in vivo. A cell-mediated immune response can be measured by various immunological assays, e.g., ELISpot, tetramer-labelling, cytotoxicity assay.

Immunogenic conjugate: A composition composed of two heterologous molecules (such as an influenza antigen and a carrier, such as a protein carrier) linked together useful for stimulating or eliciting a specific immune response (or immunogenic response) in a vertebrate. In some embodiments, the immunogenic response is protective or provides protective immunity, in that it enables the vertebrate animal to better resist infection or disease progression from the organism against which the immunogenic conjugate is directed. One specific example of a type of immunogenic conjugate is a vaccine, such as a conjugate vaccine.

Immunogenic composition: A composition useful for stimulating or eliciting a specific immune response (or immunogenic response) in a vertebrate. In some embodiments, the immunogenic response is protective or provides protective immunity, in that it enables the vertebrate animal to better resist infection or disease progression from the organism against which the immunogenic composition is directed. One specific example of a type of immunogenic composition is a vaccine.

Immunogen: A compound, composition, or substance which is capable, under appropriate conditions, of stimulating the production of antibodies or a T-cell response in an animal, including compositions that are injected or absorbed into an animal. In some examples, an immunogen is an immunogenic fragment of an influenza HA molecule.

Immunotherapy: A method of evoking an immune response against a virus (such as an influenza virus) based on their production of target antigens. Immunotherapy based on cell-mediated immune responses involves generating a cell-mediated response to cells that produce particular antigenic determinants, while immunotherapy based on humoral immune responses involves generating specific antibodies to virus that produce particular antigenic determinants.

Inhibiting or Treating a Disease: Inhibiting the full development of a disease or condition, for example, in a subject who is at risk for a disease such as an influenza viral infection. For example, inhibiting an influenza infection refers to lessening symptoms resulting from infection by the virus, such as preventing the development of symptoms in a person who is known to have been exposed to the virus or to lessening virus number or infectivity of a virus in a subject exposed to the virus. "Treatment" refers to a therapeutic intervention that ameliorates a sign or symptom of a disease or pathological condition after it has begun to develop. The term "ameliorating," with reference to a disease, pathological condition or symptom refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Isolated: An "isolated" biological component (such as a nucleic acid molecule, protein or peptide) has been substantially separated or purified away from other biological components in the cell of the organism in which the component naturally occurs, such as other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant expression in a host cell, as well as chemically synthesized nucleic acids or proteins, or fragments thereof.

Nucleic acid (molecule or sequence): A deoxyribonucleotide or ribonucleotide polymer or combination thereof including without limitation, cDNA, mRNA, genomic DNA, and synthetic (such as chemically synthesized) DNA or RNA. The nucleic acid can be double stranded (ds) or single stranded (ss). Where single stranded, the nucleic acid can be the sense strand or the antisense strand. Nucleic acids can include natural nucleotides (such as A, T/U, C, and G), and can include analogs of natural nucleotides, such as labeled nucleotides. In some examples, a nucleic acid is an influenza nucleic acid, which can include nucleic acids purified from an influenza virus as well as the amplification products of such nucleic acids or synthetically produced nucleic acids.

Nucleotide: The fundamental unit of nucleic acid molecules. A nucleotide includes a nitrogen-containing base attached to a pentose monosaccharide with one, two, or three phosphate groups attached by ester linkages to the saccharide moiety.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U).

Nucleotides include those nucleotides containing modified bases, modified sugar moieties and modified phosphate backbones, for example as described in U.S. Pat. No. 5,866,336 to Nazarenko et al.

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, and 2,6-diaminopurine amongst others.

Examples of modified sugar moieties, which may be used to modify nucleotides at any position on its structure, include, but are not limited to arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

Peptide linker: A peptide which serves to bond two heterologous amino acids sequences together, for example a immunogenic fragment of an influenza HA and a six residue histidine tag. Peptide linkers are short sequences of amino acids, such as 1, 2, 3, 4, 5, 6, 7, 8, 9, 10, 11, 12, 13, 14, 15 or ever greater than 15 amino acids in length. In some examples, a linker is peptide such as poly-lysine, poly-glutamine poly-glycine poly-proline or even combinations thereof.

Pharmaceutical agent: A chemical compound or composition capable of inducing a desired therapeutic or prophylactic effect when properly administered to a subject or a cell.

Pharmaceutically Acceptable Carriers: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds or molecules, such as one or more of the disclosed vaccines, and additional pharmaceutical agents. The term "pharmaceutically acceptable carrier" should be distinguished from "carrier" as described above in connection with an antigen/carrier conjugate.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA or RNA.

Polypeptide: A polymer in which the monomers are amino acid residues which are joined together through amide bonds. When the amino acids are alpha-amino acids, either the L-optical isomer or the D-optical isomer can be used. The term "polypeptide" is specifically intended to cover naturally occurring proteins, as well as those which are recombinantly or synthetically produced. The term "residue" or "amino acid residue" includes reference to an amino acid that is incorporated into a protein, polypeptide, or peptide.

Primers: Short nucleic acid molecules, such as a DNA oligonucleotide, for example sequences of at least 15 nucleotides, which can be annealed to a complementary target nucleic acid molecule by nucleic acid hybridization to form a hybrid between the primer and the target nucleic acid strand, such as an influenza nucleic acid. A primer can be extended along the target nucleic acid molecule by a polymerase enzyme. Therefore, primers can be used to amplify a target nucleic acid molecule (such as a portion of an influenza nucleic acid), wherein the sequence of the primer is specific for the target nucleic acid molecule, for example so that the primer will hybridize to the target nucleic acid molecule under very high stringency hybridization conditions.

The specificity of a primer increases with its length. Thus, for example, a primer that includes 30 consecutive nucleotides will anneal to a target sequence with a higher specificity than a corresponding primer of only 15 nucleotides. Thus, to obtain greater specificity, probes and primers can be selected that include at least 15, 20, 25, 30, 35, 40, 45, 50 or more consecutive nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction. PCR primer pairs can be derived from a known sequence (such as the influenza nucleic acid sequences, for example influenza HA nucleic acid sequences), for example, by using computer programs intended for that purpose such as Primer (Version 0.5, © 1991, Whitehead Institute for Biomedical Research, Cambridge, Mass.).

Methods for preparing and using primers are described in, for example, Sambrook et al. (1989) *Molecular Cloning: A Laboratory Manual*, Cold Spring Harbor, N.Y.; Ausubel et al. (1987) *Current Protocols in Molecular Biology*, Greene Publ. Assoc. & Wiley-Intersciences. In one example, a primer includes a label.

Polymerizing agent: A compound capable of reacting monomer molecules (such as nucleotides) together in a chemical reaction to form linear chains or a three-dimensional network of polymer chains. A particular example of a polymerizing agent is polymerase, an enzyme, which catalyzes the 5' to 3' elongation of a primer strand complementary to a nucleic acid template. Examples of polymerases that can be used to amplify a nucleic acid molecule include, but are not limited to the *E. coli* DNA polymerase I, specifically the Klenow fragment which has 3' to 5' exonuclease activity, Taq polymerase, reverse transcriptase (such as HIV-1 RT), *E. coli* RNA polymerase, and wheat germ RNA polymerase II.

The choice of polymerase is dependent on the nucleic acid to be amplified. If the template is a single-stranded DNA molecule, a DNA-directed DNA or RNA polymerase can be used; if the template is a single-stranded RNA molecule, then a reverse transcriptase (such as an RNA-directed DNA polymerase) can be used.

Promoter: A promoter is an array of nucleic acid control sequences that directs transcription of a nucleic acid. A promoter includes necessary nucleic acid sequences near the start site of transcription, such as in the case of a polymerase II type promoter (a TATA element). A promoter also optionally includes distal enhancer or repressor elements which can be located as much as several thousand base pairs from the start site of transcription. Both constitutive and inducible promoters are included (see e.g., Bitter et al., *Methods in Enzymology* 153:516-544, 1987).

Specific, non-limiting examples of promoters include promoters derived from the genome of mammalian cells (e.g., metallothionein promoter) or from mammalian viruses (e.g., the cytomegalovirus immediate early gene promoter, the retrovirus long terminal repeat; the adenovirus late promoter; the vaccinia virus 7.5K promoter) may be used. Promoters produced by recombinant DNA or synthetic techniques may also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Protein: A molecule, particularly a polypeptide, comprised of amino acids.

Purified: The term "purified" does not require absolute purity; rather, it is intended as a relative term. Thus, for example, a purified peptide, protein, disclosed conjugate, antigen, or other active compound is one that is isolated in whole or in part from proteins or other contaminants. Generally, substantially purified peptides, proteins, conjugates, or other active compounds for use within the disclosure comprise more than 80% of all macromolecular species present in a preparation prior to admixture or formulation of the peptide, protein, conjugate or other active compound with a pharmaceutical carrier, excipient, buffer, absorption enhancing agent, stabilizer, preservative, adjuvant or other co-ingredient in a complete pharmaceutical formulation for therapeutic administration. More typically, the peptide, protein, conjugate or other active compound is purified to represent greater than 90%, often greater than 95% of all macromolecular species present in a purified preparation prior to admixture with other formulation ingredients. In other cases, the purified preparation may be essentially homogeneous, wherein other macromolecular species are not detectable by conventional techniques. In one embodiment, a preparation is purified such that the specified component represents at least 50% (such as, but not limited to, 70%, 80%, 90%, 95%, 98% or 99%) of the total preparation by weight or volume.

Recombinant: A recombinant nucleic acid is one that has a sequence that is not naturally occurring or has a sequence that is made by an artificial combination of two otherwise separated segments of sequence, for example, a polynucleotide encoding a fusion protein. This artificial combination is often accomplished by chemical synthesis or, more commonly, by the artificial manipulation of isolated segments of nucleic acids, e.g., by genetic engineering techniques. Recombinant also can refer to the protein ("recombinant protein", such as recombinant HA and/or recombinant diphtheria toxin) produced from a recombinant nucleic acid.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (i.e., 15÷20*100=75).

One indication that two nucleic acid molecules are closely related is that the two molecules hybridize to each other under stringent conditions. Stringent conditions are sequence-dependent and are different under different environmental parameters.

Therapeutically Effective Amount: A quantity of a specified agent sufficient to achieve a desired effect in a subject being treated with that agent. For example, this may be the amount of a vaccine disclosed herein useful in increasing resistance to, preventing, ameliorating, and/or treating infection and disease caused by influenza virus infection in a subject. Ideally, a therapeutically effective amount of an agent is an amount sufficient to increase resistance to, prevent, ameliorate, and/or treat infection and disease caused by influenza virus infection in a subject without causing a substantial cytotoxic effect in the subject. The effective amount of an agent useful for increasing resistance to, preventing, ameliorating, and/or treating infection and disease caused by influenza virus infection in a subject will be dependent on the subject being treated, the severity of the affliction, and the manner of administration of the therapeutic composition.

Toxoid: A nontoxic derivative of a bacterial exotoxin produced, for example, by formaldehyde or other chemical treatment. Toxoids are useful in the formulation of immunogenic compositions because they retain most of the antigenic properties of the toxins from which they were derived.

Transduced or Transfected: A transduced cell is a cell into which a nucleic acid molecule has been introduced by molecular biology techniques. As used herein, the term introduction or transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vaccine: A vaccine is a pharmaceutical composition that elicits a prophylactic or therapeutic immune response in a subject. In some cases, the immune response is a protective response. Typically, a vaccine elicits an antigen-specific immune response to an antigen of a pathogen, for example, a bacterial or viral pathogen, or to a cellular constituent correlated with a pathological condition. A vaccine may include a polynucleotide, a peptide or polypeptide, a polysaccharide, a virus, a bacteria, a cell or one or more cellular constituents. In some cases, the virus, bacteria or cell may be inactivated or attenuated to prevent or reduce the likelihood of infection, while maintaining the immunogenicity of the vaccine constituent.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker gene and other genetic elements known in the art. The term vector includes plasmids, linear nucleic acid molecules.

II. Description of Several Embodiments

Influenza A virus causes annual epidemics of acute respiratory disease and worldwide pandemics. The lipid envelope surface of the virus is covered with approximately 1000 protruding protein spikes each consisting of three identical hemagglutinin (HA) molecules. Serum IgG against these spikes (anti-HA) neutralizes viral infectivity. The segmented viral genome is negative, single-stranded RNA. Genetic mutations are acquired during replication by the virus encoded, error-prone RNA polymerase. Mutations beneficial to viral survival, such as eluding the host immune defenses, are conserved by the evolving virus. Genetic drift mutations in the gene encoding the HA protein necessitate frequent changes of vaccines in order to be effective against the rapidly evolving virus.

Although uncommon, a major genetic shift can occur by reassortment of the segmented RNA genome leading to a change in the circulating sub-type in humans, potentially causing a pandemic. Currently, 16 sub-types of HA have been identified in avian influenza A viruses, three of which are also identified in human strains.

The speed of vaccine production, especially for potential pandemic viruses, is limited by current manufacturing processes. Each year, circulating virus strains are characterized by RNA sequence and immunological cross-reactivity with other strains. From these data, candidate strains are identified and released to vaccine manufacturers. The majority of influenza manufacturing relies on embryonated chicken eggs to propagate the vaccine virus. If the circulating virus strain is not lethal to eggs, it is grown in eggs, purified, inactivated chemically, tested and then distributed. Highly pathogenic strains that cannot be grown in eggs require genetic modification, which prolongs the production schedule. Typically the current vaccine production process produces only enough vaccine for one dose per person and is not available until just before the flu season begins in the fall. To put this number in perspective, the peak of the 1918 influenza pandemic lasted only four months and resulted in 50 to 100 million deaths. Thus, innovative vaccines and methods for rapid production of influenza vaccines are urgently needed.

The current disclosure meets those needs by providing immunogenic compositions, such as vaccines, that are useful in the treatment and/or inhibition of influenza infection. Also disclosed are methods of rapidly producing influenza vaccines to meet the threats posed by global influenza pandemics.

A. M2e Vaccines

It has been shown that antibodies to the exposed N-terminal 23 amino acids of the mature influenza matrix 2 protein (M2) ectodomain (M2e) may ameliorate influenza disease symptoms. The M2 protein provides an ion-channel through the viral membrane and is recognized as a target for prophylaxis and treatment with the antiviral drug, AMANTADINE®. Unlike the virions surface proteins, HA and NA, which are subject to constant genetic drift and shift, the M2 protein is highly conserved. This is likely due to its protected location within the viral membrane, preventing a strong host immune response. To exploit this conservation in sequence and provide a "universal" influenza vaccine, disclosed are novel M2e immunogenic conjugates that are able to confer a protective immune response to challenge by influenza infection.

The disclosed immunogenic conjugates include M2 ectodomain (M2e) peptide covalently linked to a carrier by a thioether linkage and are represented by the general formula:

M2e-Cys-S—$CH_2$—C(O)—NH—$CH_2$—CH2-C
(O—)—NH-Lys-Pr, where M2e is the influenza M2 ectodomain (M2e) peptide; Cys is a cysteine amino acid residue introduced at the C-terminal end of the M2e peptide; S the sulfur present in the cysteine amino acid residue; CH2-CO—NH—CH2-CH2-CO the linking group; NH the amine group present in a lysine residue of the carrier protein; Lys is a lysine amino acid residue present in the carrier protein and Pr the carrier protein. A generalized scheme for introducing a thioether linkage between a cysteine amino acid residue and a lysine amino acid residue is described in Kubler-Kielb et al. *Infection and Immunity* 74(8): 4744-4749, 2006, which is incorporated herein by reference in its entirety. An exemplary scheme for the conjugation of an M2e peptide to a carrier protein via a thioether linkage is shown in FIG. 1

As detailed in the Examples below, such an immunogenic conjugate is capable of eliciting an immune response in a subject. The M2e and carrier shall be described in more detail below. Any specific combination of M2e and carrier may be selected from the specific M2e and carriers that are listed below.

Figure 5:
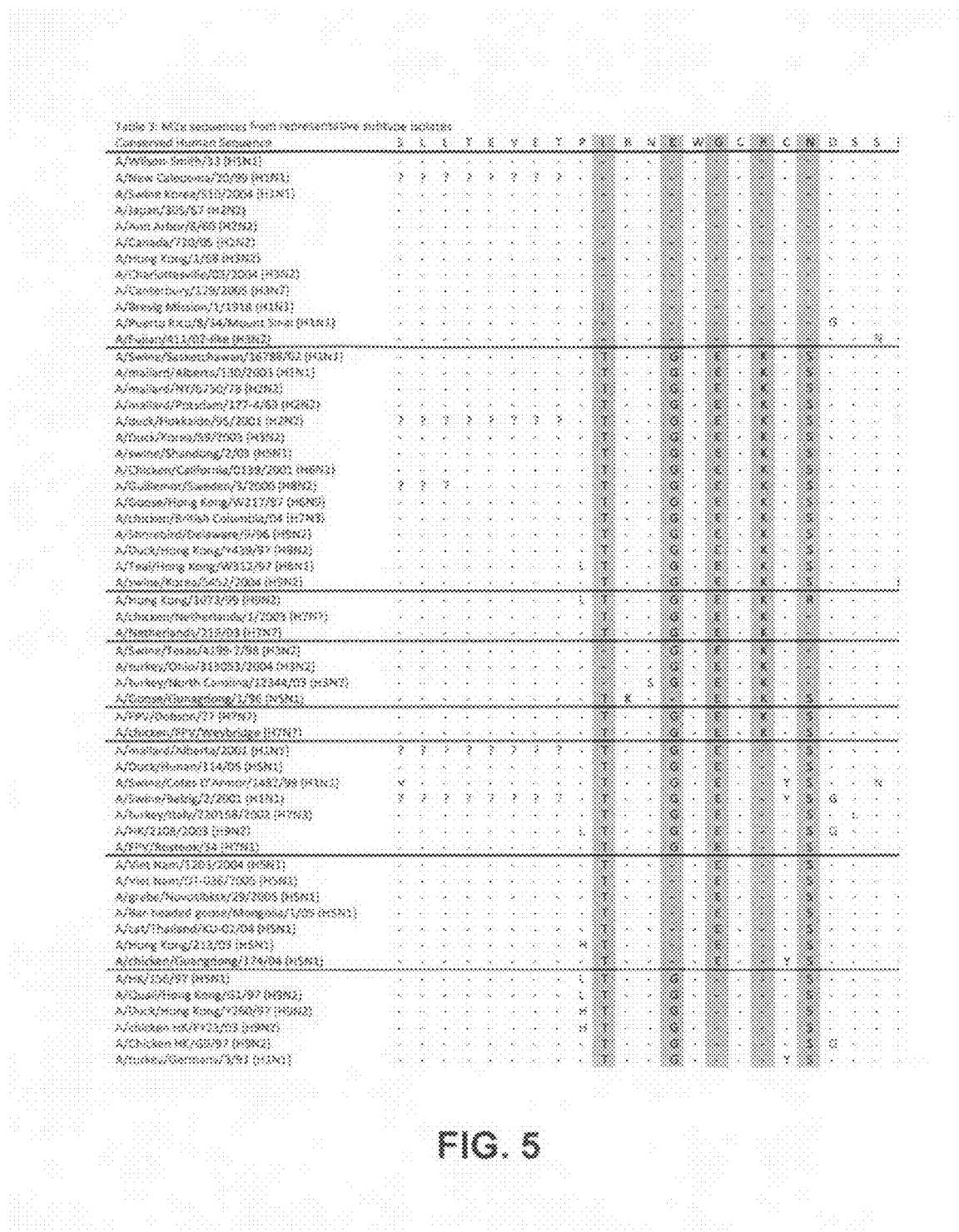

Table 3 given in FIG. 5, shows an alignment of M2e sequences from representative influenza virus subtype isolates as compared to a conserved human M2e sequence (SEQ ID NO: 5) that is 23 amino acids in length. Table 3 also shows several amino acid substitutions in the M2e amino acid sequence that have, been found in influenza isolates. The substitutions are made relative to SEQ ID NO: 5.

To allow for the conjugation of the M2e peptide to carrier proteins containing a lysine amino acid residue via a thioether linkage, a cysteine reside was engineered into the C-terminal end of the M2e peptide, yielding a peptide 24 amino acids in length. The consensus sequence for the M2e peptide included in the immunogenic conjugates of this disclosure is set forth as $X_1$LLTEVET$X_2X_3X_4X_5X_6$W$X_7$C$X_8X_9X_{10}X_{11}X_{12}$ $X_{13}X_{14}$C (SEQ ID NO: 3), where $X_1$ can be serine or valine; $X_2$ can be proline, leucine or histidine; $X_3$ can be isoleucine or threonine; $X_4$ can be arginine or lysine; $X_5$ can be asparigine or serine; $X_6$ can be glutamic acid or glycine; $X_7$ can be glycine or glutamic acid; $X_8$ can be arginine or lysine; $X_9$ can be cysteine or tyrosine; $X_{10}$ can be glutamine or serine; $X_{11}$ can be aspartic acid or glycine; $X_{12}$ can be serine or leucine; $X_{13}$ can be serine or arginine; and $X_{14}$ can be aspartic acid or glutamic acid.

In some embodiments, a disclosed immunogenic conjugate includes an M2e peptide that comprises the amino acid sequence set forth as $X_1$LLTEVET$X_2X_3X_4X_5$ $X_6$W$X_7$C$X_8X_9X_{10}X_{11}X_{12}X_{13}X_{14}$C (SEQ ID NO: 3), where $X_1$ can be serine or valine; $X_2$ can be proline, leucine or histidine; $X_3$ can be isoleucine or threonine; $X_4$ can be arginine or lysine; $X_5$ can be asparigine or serine; $X_6$ can be glutamic acid or glycine; $X_7$ can be glycine or glutamic acid; $X_8$ can be arginine or lysine; $X_9$ can be cysteine or tyrosine; $X_{10}$ can be glutamine or serine; $X_{11}$ can be aspartic acid or glycine; $X_{12}$ can be serine or leucine; $X_{13}$ can be serine or arginine; and $X_{14}$ can be aspartic acid or glutamic acid.

In some embodiments, a disclosed immunogenic conjugate includes an M2e peptide that comprises the amino acid sequence set forth as SLLTEVETPIRNEWGCRCNDSSD (SEQ ID NO: 4).

It may be advantageous to produce conjugates in which more than one M2e peptide is conjugated to a single carrier protein, for example multiple copies of an M2e peptide a single amino acid sequence or several different M2e peptides with different amino acid sequences (or multiple copies of several different M2e peptides). The conjugation of multiple M2e peptides to a single carrier protein is possible because the carrier protein has multiple lysine sidechains that can serve as sites of attachment. The amount of M2e peptide reacted with the amount of carrier may vary depending upon the specific M2e peptide and the carrier protein. However, the respective amounts should be sufficient to introduce about 1-20 chains of M2e peptide onto the carrier protein. The resulting number of M2e peptides bound to a single protein carrier molecule may vary depending upon the specific M2e and the carrier protein, but in general, about 1 to about 20, such as about 1, about 2, about 3, about 4, about 5, about 6, about 7, about 8, about 9, about 10, about 11, about 12, about 13, about 14, about 15, about 16, about 17, about 18, about 19, about 20 or even more than 20 M2e peptides chains can be bound to each carrier protein molecule. Thus, the average ratio of M2e peptide molecules to carrier protein molecules is between about 1:1 and about 20:1, such as about 2:1, about 3:1, about 4:1, about 5:1, about 6:1, about 7:1, about 8:1, about 9:1, about 10:1, about 11:1, 12:1, about 13:1, about 14:1, about 15:1, about 16:1, about 17:1, about 18:1, about 19:1, or about 20:1, for example, between about 1:1 and about 15:1, between about 5:1 and about 10:1, between about 6:1 and about 7:1, or even about 6.5:1.

Examples of suitable carriers are those that can increase the immunogenicity of the conjugate and/or elicit antibodies against the carrier which are diagnostically, analytically, and/or therapeutically beneficial. Useful carriers include polymeric carriers, which can be natural, recombinantly produced, semi-synthetic or synthetic materials containing one or more amino groups, such as those present in a lysine amino acid residue present in the carrier, to which a reactant moiety can be attached. Carriers that fulfill these criteria are generally known in the art (see, for example, Fattom et al., *Infect. Immun.* 58:2309-12, 1990; Devi et al., *PNAS* 88:7175-79, 1991; Szu et al., *Infect. Immun.* 59:4555-61, 1991; Szu et al., *J. Exp. Med.* 166:1510-24, 1987; and Pavliakova et al., *Infect.*

*Immun.* 68:2161-66, 2000). A carrier can be useful even if the antibody that it induces is not of benefit by itself.

Specific, non-limiting examples of suitable polypeptide carriers include, but are not limited to, natural, semi-synthetic or synthetic polypeptides or proteins from bacteria or viruses. In one embodiment, bacterial products for use as carriers include bacterial toxins. Bacterial toxins include bacterial products that mediate toxic effects, inflammatory responses, stress, shock, chronic sequelae, or mortality in a susceptible host. Specific, non-limiting examples of bacterial toxins include, but are not limited to: *B. anthracis* PA (for example, as encoded by bases 143779 to 146073 of GENBANK® Accession No. NC 007322), including variants that share at least 90%, at least 95%, or at least 98% amino acid sequence homology to PA, fragments that contain at least one antigenic epitope, and analogs or derivatives capable of eliciting an immune response; *B. anthracis* LF (for example, as encoded by the complement of bases 149357 to 151786 of GEN-BANK® Accession No. NC 007322); bacterial toxins and toxoids, such as tetanus toxin/toxoid (for example, as described in U.S. Pat. Nos. 5,601,826 and 6,696,065); diphtheria toxin/toxoid (for example, as described in U.S. Pat. Nos. 4,709,017 and 6,696,065), detoxified mutant diphtheria toxin, for example the genetically detoxified diphtheria toxin wherein the histidine at position 21 is replaced with glycine (DT-H21G) as described by Kossaczka et al. *Infect Immun.* 2000 September; 68(9): 5037-5043; *P. aeruginosa* exotoxin/toxoid/(for example, as described in U.S. Pat. Nos. 4,428,931, 4,488,991 and 5,602,095); pertussis toxin/toxoid (for example, as described in U.S. Pat. Nos. 4,997,915, 6,399,076 and 6,696,065); and *C. perfringens* exotoxin/toxoid (for example, as described in U.S. Pat. Nos. 5,817,317 and 6,403,094). Viral proteins, such as hepatitis B surface antigen (for example, as described in U.S. Pat. Nos. 5,151,023 and 6,013,264) and core antigen (for example, as described in U.S. Pat. Nos. 4,547,367 and 4,547,368) can also be used as carriers, as well as proteins from higher organisms such as keyhole limpet hemocyanin, horseshoe crab hemocyanin, edestin, mammalian serum albumins, and mammalian immunoglobulins. Exemplary methods for the conjugation of M2e peptides with carriers are described in the Examples and specifically Example 1. In a specific example, the M2e peptide is conjugated to detoxified mutant diphtheria toxin, wherein the histidine at position 21 is replaced with glycine (DT-H21G).

Following conjugation of the M2e peptide to a carrier protein, the conjugate can be purified by a variety of techniques well known to one of skill in the art. One goal of the purification step is to remove the unbound M2e or carrier from the conjugate. One method for purification, involving ultrafiltration in the presence of ammonium sulfate, is described in U.S. Pat. No. 6,146,902. Alternatively, the conjugates can be purified away from unreacted hapten/antigen and carrier by any number of standard techniques including, for example, size exclusion chromatography, density gradient centrifugation, hydrophobic interaction chromatography, or ammonium sulfate fractionation. See, for example, Anderson et al., *J. Immunol.* 137:1181-86, 1986 and Jennings & Lugowski, *J. Immunol.* 127:1011-18, 1981. The compositions and purity of the conjugates can be determined by GLC-MS and MALDI-TOF spectrometry.

The disclosed immunogenic conjugates can be formulated into immunogenic composition (such as vaccines), for example by the addition of a pharmaceutically acceptable carrier and/or adjuvant. The formulation of immunogenic compositions is detailed below in subsection C.

B. HA Vaccines

Disclosed herein are methods for recombinantly producing HA (rHA) vaccines in a bacterial culture system, such as an *E. coli* bacterial culture system. Because the methods only use viral sequence data or a small sample of viral RNA, one of the many advantages of this system is the elimination of handling potentially lethal virus. In addition, because a bacterial culture system is used, potential vaccine candidates can be produced and tested in less than 3 to 4 weeks.

Four unique features were incorporated into the rHA immunogen: 1) removal of the signal or leader sequence, which is not a part of the mature HA0 protein. 2) truncation of the C-terminal domain which transverses virus capsid region and terminates within the virus particle. This truncated region is not important immunologically and it interferes with purification of the HA. 3) replacement of the truncated region with a His-tag to facilitate rapid purification. 4) inclusion of the polybasic amino acid region located at the HAVHA2 host proteinase cleavage site. The polybasic amino acid site is an important characteristic of highly pathogenic avian influenza H5N1 viruses because it is essential for virus activation and entry into the host cell. By necessity, highly pathogenic virus strains supplied to vaccine developers and manufacturers have the polybasic amino acid site removed to provide a margin of safety during manufacturing processes. Because, the disclosed method produces rHA immunogen with the polybasic amino acid site intact rapidly and safely, it has the added advantage of producing antigens that represent fully this essential viral activation site. For example, antibodies that bind to the fusion peptide sequence immediately following the polybasic amino acid protease cleavage site can protect against lethal H5N1 viral infection. It has also been shown that antibodies that bind to a highly conserved epitope within a pocket in the HA stem region can neutralize virus infectivity. This pocket is comprised of the conserved fusion peptide as well as the polybasic protease cleavage site. Structural hindrance around the conserved epitope may limit its ability to induce antibody production or the ability of an antibody to effectively bind to the epitope. However, if antibodies can bind to amino acid residues within the conserved pocket and block protease cleavage, infectivity will be reduced since the virus cannot infect the host cell without the released HA2 fusion peptide to interact with the host membrane.

Disclosed are methods of producing an influenza vaccine specific for an identified influenza strain. A nucleic acid sequence of the identified influenza strain encoding a hemagglutinin (HA) from the identified influenza strain is obtained, for example from the known sequence of the HA gene (such as those available on the world wide web at ncbi.nlm.nih.gov/entrez) or the Influenza Sequence Database of Los Alamos National Laboratories (LANL) (available on the world wide web at flu.lanl.gov) or by sequencing. Once obtained, a nucleic acid molecule encoding an immunogenic fragment of the HA, wherein the nucleic acid molecule produced encodes the polybasic cleavage site, and wherein the nucleic acid molecule produced does not encode a leader sequence at the N-terminal end of immunogenic fragment of the HA or a transmembrane domain at the C-terminal end of immunogenic fragment of the HA. The nucleic acid molecule can be produced by a variety of methods known to those of ordinary skill in the art, for example by synthetically producing the nucleic acid sequence using readily available DNA synthesis technology or generally known cloning techniques. An immunogenic fragment of the HA is expressed from the nucleic acid molecule in a bacterial expression system (such as an *E. coli* expression system) and the expressed immunogenic fragment of the HA is purified, thereby producing an influenza vaccine specific for an identified influenza strain. Methods of recombinantly producing proteins and peptides, such as rHA proteins are given below in subsection E.

In some embodiments of the disclosed methods, the purified immunogenic fragment of the influenza HA protein is adsorbed onto alum, for example to increase the immunogenicity of the purified immunogenic fragment of the influenza HA protein. In some embodiments, the immunogenic fragment of the influenza HA protein is treated with a fixative, such as a crosslinking agent, for example an aldehyde crosslinking agent such as formalin.

In some examples, the nucleic acid molecule encoding an immunogenic fragment of the HA is codon optimized for expression in *E. coli*.

In some example, the immunogenic fragment of an influenza HA protein comprises a six residue histidine tag linked by a peptide linker, such as a Gly-Gly-Gly, peptide linker to the C-terminal end of the immunogenic fragment of the influenza HA protein. The inclusion of a C-terminal six residue histidine tag facilitates purification of the immunogenic fragment of an influenza HA protein.

Also disclosed are immunogenic compositions that include an isolated immunogenic fragment of an influenza HA protein including the polybasic cleavage site, wherein the immunogenic fragment of the influenza HA protein has been modified to remove an N-terminal leader amino acid sequence and a C-terminal transmembrane domain. In some examples, the immunogenic fragment of the influenza HA protein is not glycosylated. In some examples, the immunogenic fragment of an influenza HA protein comprises a six residue histidine tag linked by a peptide linker (such as a Gly-Gly-Gly peptide linker) to the C-terminal end of the immunogenic fragment of the influenza HA protein.

In some embodiments, the immunogenic composition further comprises an adjuvant, such as alum, and the immunogenic fragment of the influenza HA protein is adsorbed onto the alum.

In some embodiment, the immunogenic fragment of the influenza HA protein is treated with a fixative, such as a crosslinking agent, for example an aldehyde crosslinking agent such as formalin.

Using viral RNA and recombinant DNA technology, the methods described in this section were used to produce a recombinant H5N1 Vietnam HA suitable for vaccine safely, in a short time and with high yield as is described in the Examples Section. The amino acid sequence of this construct is set forth as:

```
                                           (SEQ ID NO: 6)
MGDQICIGYH ANNSTEQVDT IMEKNVTVTH AQDILEKKHN

GKLCDLDGVK PLILRDCSVA GWLLGNPMCD EFINVPEWSY

IVEKANPVND LCYPGDFNDY EELKHLLSRI NHFEKIQIIP

KSSWSSHEAS LGVSSACPYQ GKSSFFRNVV WLIKKNSTYP

TIKRSYNNTN QEDLLVLWGI HHPNDAAEQT KLYQNPTTYI

SVGTSTLNQR LVPRIATRSK VNGQSGRMEF FWTILKPNDA

INFESNGNFI APEYAYKIVK KGDSTIMKSE LEYGNCNTKC

QTPMGAINSS MPFHNIHPLT IGECPKYVKS NRLVLATGLR

NSPQRERRRK KRGLFGAIAG FIEGGWQGMV DGWYGYHHSN

EQGSGYAADK ESTQKAIDGV TNKVNSIIDK MNTQFEAVGR
```

```
                         -continued
EFNNLERRIE NLNKKMEDGF LDVWTYNAEL LVLMENERTL

DFHDSNVKNL YDKVRLQLRD NAKELGNGCF EFYHKCDNEC

MESVRNGTYD YPQYSEEARL KREEISGVKL ESIGIYQGGG

HHHHHH.
```

The N-terminal Met-Gly (bolded) was added to facilitate cloning and expression and the C-terminal 3×Gly and 6×His were added to facilitate purification. The position of the polybasic cleavage site is shown as bolded italics.

The recombinant protein expressed in *E. coli* was nonglycosylated and its molecular weight and antigenic characteristics conformed to those of influenza HA. It was immunogenic by itself, showed booster and dose responses and alum adsorption increased the antibody levels. The rHA-induced antibodies demonstrated HI activity though the titers did not correlate with ELISA levels, consistent with findings of other investigators. However, the HI activity is consistent with the FDA guidelines for vaccines against epidemic and pandemic influenza. As of the filing of this disclosure rHA from the A/Indonesia/5/2005 influenza (H5N1) strain, A/Qinghai/1A/2005 (H5N1) strain, and the A/California/04/2009 (H1N1) pandemic swine strain are being produced and undergoing testing and evaluation.

The disclosed immunogenic fragments of HA can be further formulated into immunogenic composition (such as vaccines), for example by the addition of a pharmaceutically acceptable carrier and/or adjuvant. The formulation of immunogenic compositions is detailed below in subsection C.

C. Therapeutic Formulations.

The immunogenic compositions or vaccines disclosed herein may be included in pharmaceutical compositions (including therapeutic and prophylactic formulations), typically combined together with one or more pharmaceutically acceptable vehicles and, optionally, other therapeutic ingredients (for example, antibiotics or antiviral drugs).

Such pharmaceutical compositions can be administered to subjects by a variety of mucosal administration modes, including by oral, rectal, intranasal, intrapulmonary, or transdermal delivery, or by topical delivery to other surfaces. Optionally, the immunogenic compositions can be administered by non-mucosal routes, including by intramuscular, subcutaneous, intravenous, intra-arterial, intra-articular, intraperitoneal, or parenteral routes. Alternatively, the vaccine can be administered ex vivo by direct exposure to cells, tissues or organs originating from a subject.

To formulate the pharmaceutical compositions, the vaccine can be combined with various pharmaceutically acceptable additives, as well as a base or vehicle for dispersion of the conjugate. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, TWEEN® 80), solubility enhancing agents (for example, cyclodextrins and derivatives thereof), stabilizers (for example, serum albumin), and reducing agents (for example, glutathione) can be included. Adjuvants, such as aluminum hydroxide (for example, AMPHO-GEL®, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions.

When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The vaccine can be dispersed in a base or vehicle, which can include a hydrophilic compound having a capacity to disperse the vaccine, and any desired additives. The base can be selected from a wide range of suitable compounds, including but not limited to, copolymers of polycarboxylic acids or salts thereof, carboxylic anhydrides (for example, maleic anhydride) with other monomers (for example, methyl(meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The vaccine can be combined with the base or vehicle according to a variety of methods, and release of the vaccine can be by diffusion, disintegration of the vehicle, or associated formation of water channels. In some circumstances, the vaccine is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the vaccine can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the vaccine can be brought about by including in the composition an agent which delays absorption, for example, monostearate salts and gelatin.

In certain embodiments, the vaccine can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the vaccine and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly(epsilon-caprolactone), poly(epsilon-aprolactone-CO-lactic acid), poly(epsilon.-aprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the conjugate in the required amount in an appropriate solvent with one or a combination of ingredients enumerated herein, as required, followed by filtered sterilization. Generally, dispersions are prepared by incorporating the vaccine and/or other biologically active agent into a sterile vehicle that contains a basic dispersion medium and the required other ingredients from those enumerated herein. In the case of sterile powders, methods of preparation include vacuum drying and freeze-drying which yields a powder of the vaccine plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

D. Methods of Treatment

In accordance with the various treatment methods of the disclosure, the disclosed immunogenic compositions or vaccines can be delivered to a subject in a manner consistent with conventional methodologies associated with management of the disorder for which treatment or prevention is sought, for example infection from influenza virus. In accordance with the disclosure herein, a prophylactically or therapeutically effective amount of the immunogenic composition and/or other biologically active agent is administered to a subject in need of such treatment for a time and under conditions sufficient to prevent, inhibit, and/or ameliorate a selected disease or condition or one or more symptom(s) thereof. In some embodiments, administration of the disclosed vaccines to a subject elicits an immune response against an influenza antigenic epitope in the subject, for example an immune response against an influenza M2 protein or an influenza HA protein. In some embodiments, a subject is selected for treatment that has, or is at risk for developing, an influenza infection, for example because of exposure or the possibility of exposure to influenza. Alternatively, the subject is selected because of risk factors for infection and/or morbidity (for example the subject is very young or old, pregnant, immunocompromised or suffering from a chronic pulmonary condition)

Typical subjects intended for treatment with the compositions and methods of the present disclosure include humans, as well as non-human primates and other animals. To identify subjects for prophylaxis or treatment according to the methods of the disclosure, accepted screening methods are employed to determine risk factors associated with a targeted or suspected disease of condition (for example, coughing disease) as discussed herein, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods, which are available and well known in the art to detect and/or characterize disease-associated markers. These and other routine methods allow the clinician to select patients in need of therapy using the methods and pharmaceutical compositions of the disclosure. In accordance with these methods and principles, a vaccine and/or other biologically active agent can be administered according to the teachings herein as an independent prophylaxis or treatment program, or as a follow-up, adjunct or coordinate treatment regimen to other treatments.

The vaccine can be used in coordinate vaccination protocols or combinatorial formulations. In certain embodiments, novel combinatorial immunogenic compositions and coordinate immunization protocols employ separate immunogens or formulations, each directed toward eliciting an anti-influenza immune response, such as an immune response to influenza HA or M protein. Separate vaccines that elicit the anti-influenza immune response can be combined in a polyvalent immunogenic composition administered to a subject in a single immunization step, or they can be administered separately (in monovalent immunogenic compositions) in a coordinate immunization protocol. For example, a disclosed M2e vaccine and a disclosed HA based vaccine can be administered together or separately according to the teaching present in this disclosure.

The administration of the vaccines of the disclosure can be for either prophylactic or therapeutic purpose. When provided prophylactically, the vaccine is provided in advance of any symptom, for example in advance of infection, such as in the form of a yearly flu shot. The prophylactic administration of the vaccine serves to prevent or ameliorate any subsequent infection. When provided therapeutically, the vaccine is provided at (or shortly after) the onset of a symptom of disease or infection. The vaccine of the disclosure can thus be provided prior to the anticipated exposure to influenza virus so as to attenuate the anticipated severity, duration or extent of an infection and/or associated disease symptoms, after exposure or suspected exposure to the virus, or after the actual initiation of an infection.

For prophylactic and therapeutic purposes, the vaccine can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the vaccine can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, ferret, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the vaccine (for example, amounts that are effective to elicit a desired immune response or alleviate one or more symptoms of a targeted disease). In alternative embodiments, an effective amount or effective dose of the vaccine may simply inhibit or enhance one or more selected biological activities correlated with a disease or condition, as set forth herein, for either therapeutic or diagnostic purposes.

The actual dosage of the vaccine will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the vaccine for eliciting the desired activity or biological response in the subject. Dosage regimens can be adjusted to provide an optimum prophylactic or therapeutic response. As described above in the forgoing listing of terms, a therapeutically effective amount is also one in which any toxic or detrimental side effects of the vaccine and/or other biologically active agent is outweighed in clinical terms by therapeutically beneficial effects. A non-limiting range for a therapeutically effective amount of a vaccine and/or other biologically active agent within the methods and formulations of the disclosure is about 0.01 mg/kg body weight to about 10 mg/kg body weight, such as about 0.05 mg/kg to about 5 mg/kg body weight, or about 0.2 mg/kg to about 2 mg/kg body weight.

Upon administration of a vaccine of the disclosure (for example, via injection, aerosol, oral, topical or other route), the immune system of the subject typically responds to the immunogenic composition by producing antibodies specific for influenza proteins, such as the M2 protein and/or the HA protein and/or an antigenic epitope presented by the vaccine. Such a response signifies that an immunologically effective dose of the vaccine was delivered. An immunologically effective dosage can be achieved by single or multiple administrations (including, for example, multiple administrations per day), daily, or weekly administrations. For each particular subject, specific dosage regimens can be evaluated and adjusted over time according to the individual need and professional judgment of the person administering or supervising the administration of the vaccine. In some embodiments, the antibody response of a subject administered the compositions of the disclosure will be determined in the context of evaluating effective dosages/immunization protocols. In most instances it will be sufficient to assess the antibody titer in serum or plasma obtained from the subject. Decisions as to whether to administer booster inoculations and/or to change the amount of the composition administered to the individual can be at least partially based on the antibody titer level. The antibody titer level can be based on, for example, an immunobinding assay which measures the concentration of antibodies in the serum which bind to a specific antigen, for example, influenza M2 protein and/or HA protein.

Dosage can be varied by the attending clinician to maintain a desired concentration at a target site (for example, the lungs or systemic circulation). Higher or lower concentrations can be selected based on the mode of delivery, for example, transepidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth. To achieve the same serum concentration level, for example, slow-release particles with a release rate of 5 nanomolar (under standard conditions) would be administered at about twice the dosage of particles with a release rate of 10 nanomolar.

The methods of using vaccines, and the related compositions and methods of the disclosure are useful in increasing resistance to, preventing, ameliorating, and/or treating infection and disease caused by influenza virus in animal hosts, and other, in vitro applications. These immunogenic compositions can be used for active immunization for prevention of infection, and for preparation of immune antibodies. The immunogenic compositions are composed of non-toxic components, suitable for infants, children of all ages, and adults.

This disclosure also includes kits, packages and multi-container units containing the herein described pharmaceutical compositions, active ingredients, and/or means for administering the same for use in the prevention and treatment of influenza and other conditions in mammalian subjects. Kits for diagnostic use are also provided. In one embodiment, these kits include a container or formulation that contains one or more of the conjugates described herein. In one example, this component is formulated in a pharmaceutical preparation for delivery to a subject. The vaccine is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

E. Peptide or Protein Production

Nucleic acid molecules encoding the M2e, HA peptides, carrier proteins, and any other peptides or proteins of this disclosure can be prepared by cloning techniques. Examples of appropriate cloning and sequencing techniques, and instructions sufficient to direct persons of skill through many cloning exercises are found in Sambrook et al., *Molecular Cloning: A Laboratory Manual* (2nd Ed.), Vols. 1-3, Cold Spring Harbor Laboratory (1989), Berger and Kimmel (eds.), *Guide to Molecular Cloning Techniques*, Academic Press, Inc., San Diego Calif. (1987), or Ausubel et al. (eds.), *Current Protocols in Molecular Biology*, Greene Publishing and Wiley-Interscience, NY (1987). Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH® laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), INVITROGEN™ (San Diego, Calif.), and Applied Biosystems (Foster City, Calif.), as well as many other commercial sources known to one of skill.

In some embodiments, the peptides of this disclosure are produced recombinantly, for example from cells transformed or transfected with polynucleotides encoding the peptides or portion thereof. Methods for the manipulation and insertion of the nucleic acids encoding the peptides of this disclosure or portions thereof into vectors for the expression of polypeptides are well known in the art (see for example, Sambrook et al., *Molecular Cloning, a Laboratory Manual*, 2d edition, Cold Spring Harbor Press, Cold Spring Harbor, N.Y., 1989, and Ausubel et al., *Current Protocols in Molecular Biology*, Greene Publishing Associates and John Wiley & Sons, New York, N.Y., 1994).

The nucleic acid sequences encoding M2e, immunogenic fragments of HA peptides, carrier proteins, and any other peptides or proteins of this disclosure can be operatively linked to expression control sequences. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (for instance, ATG) in front of a protein-encoding gene, splicing signal for introns, maintenance of the correct reading frame of that gene to permit proper translation of mRNA, and stop codons.

Transformation of a host cell with recombinant DNA may be carried out by conventional techniques as are well known to those skilled in the art. Where the host is prokaryotic, such as *E. coli*, competent cells, which are capable of DNA uptake can be prepared from cells harvested after exponential growth phase and subsequently treated by the $CaCl_2$ method using procedures well known in the art. Alternatively, $MgCl_2$, or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding M2e peptides and/or carrier proteins and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Eukaryotic Viral Vectors, Cold Spring Harbor Laboratory, Gluzman ed., 1982).

The expression and purification of any of these M2e, immunogenic fragments of HA peptides, carrier proteins, and any other peptides or proteins of this disclosure by standard laboratory techniques, is now enabled. Fragments amplified as described herein can be cloned into standard cloning vectors and expressed in commonly used expression systems consisting of a cloning vector and a cell system in which the vector is replicated and expressed. Purified proteins may be used for functional analyses, antibody production, diagnosis, and subject therapy. Partial or full-length cDNA sequences, which encode for the protein, may be ligated into bacterial expression vectors. Methods for expressing large amounts of protein from a cloned gene introduced into *E. coli* may be utilized for the purification of proteins.

M2e peptides, immunogenic fragments of HA peptides, carrier proteins, and any other peptides or proteins of this disclosure may also be produced in *E. coli* in large amounts for vaccine development and/or evaluation. Standard prokaryotic cloning vectors may also be used, for example, pBR322, pUC18, or pUC19 as described in Sambrook et al. (Molecular Cloning: A Laboratory Manual, $2^{nd}$ ed., vol. 1-3, Cold Spring Harbor, N.Y. 1989). Nucleic acids encoding M2e peptides, immunogenic fragments of HA peptides, carrier proteins, and any other peptides or proteins of this disclosure may be cloned into such vectors, which may then be transformed into bacteria such as *E. coli*, which may then be cultured to express the protein of interest. Other prokaryotic expression systems include, for instance, the arabinose-induced pBAD expression system that allows tightly controlled regulation of expression, the IPTG-induced pRSET system that facilitates rapid purification of recombinant proteins and the IPTG-induced pSE402 system that has been constructed for optimal translation of eukaryotic genes. These three systems are available commercially from INVITROGENT™ and, when used according to the manufacturer's instructions, allow routine expression and purification of proteins.

Methods and plasmid vectors for producing proteins and peptides in bacteria are described in Sambrook et al. (Molecular Cloning: A Laboratory Manual, Cold Spring Harbor, N.Y., 1989, Chapter 17). Such proteins and peptides may be made in large amounts, are easy to purify, and can be used to elicit antibody response. Proteins and proteins can be produced in bacteria by placing a strong, regulated promoter and an efficient ribosome binding site upstream of the cloned gene. If low levels of protein are produced, additional steps may be taken to increase protein production; if high levels of protein are produced, purification is relatively easy. Suitable methods are presented in Sambrook et al. (Molecular Cloning: A Laboratory Manual, Cold Spring Harbor, N.Y., 1989) and are well known in the art. Often, proteins expressed at high levels are found in insoluble inclusion bodies. Methods for extracting proteins from these aggregates are described by Sambrook et al. (Molecular Cloning: A Laboratory Manual, Cold Spring Harbor, N.Y., 1989, Chapter 17).

Vector systems suitable for the expression of proteins and peptides include the pUR series of vectors (Ruther and Muller-Hill, *EMBO J.* 2:1791, 1983), pEX1-3 (Stanley and Luzio, *EMBO J.* 3:1429, 1984) and pMR100 (Gray et al., *Proc. Natl. Acad. Sci. USA* 79:6598, 1982). Vectors suitable for the production of intact native proteins include pKC30 (Shimatake and Rosenberg, *Nature* 292:128, 1981), pKK177-3 (Amann and Brosius, *Gene* 40:183, 1985) and pET-3 (Studiar and Moffatt, *J. Mol. Biol.* 189:113, 1986). The DNA sequence can also be transferred to other cloning vehicles, such as other plasmids, bacteriophages, cosmids, animal viruses, and yeast artificial chromosomes (YACs) (Burke et al., *Science* 236:806-12, 1987). These vectors may then be introduced into a variety of hosts including somatic cells, and simple or complex organisms, such as bacteria, fungi (Timberlake and Marshall, *Science* 244:1313-7, 1989), invertebrates, plants (Gasser and Fraley, Science 244:1293, 1989), and mammals (Pursel et al., *Science* 244:1281-8, 1989).

Various yeast strains and yeast-derived vectors are commonly used for expressing and purifying proteins, for example, *Pichia pastoris* expression systems are available from INVITROGENT™ (Carlsbad, Calif.). Such systems include suitable *Pichia pastoris* strains, vectors, reagents, transformants, sequencing primers and media.

Non-yeast eukaryotic vectors can also be used for expression of the M2e peptides. Examples of such systems are the well known Baculovirus system, the Ecdysone-inducible mammalian expression system that uses regulatory elements from *Drosophila melanogaster* to allow control of gene expression, and the Sindbis viral expression system that allows high level expression in a variety of mammalian cell lines. These expression systems are available from INVITROGENT™.

For expression in mammalian cells, the cDNA sequence may be ligated to heterologous promoters, such as the simian virus SV40, promoter in the pSV2 vector (Mulligan and Berg, 1981, *Proc. Natl. Acad. Sci. USA* 78:2072-6), and introduced into cells, such as monkey COS-1 cells (Gluzman, *Cell* 23:175-82, 1981), to achieve transient or long-term expression. The stable integration of the chimeric gene construct may be maintained in mammalian cells by biochemical selection, such as neomycin (Southern and Berg, *J. Mol. Appl. Genet.* 1:327-41, 1982) and mycophoenolic acid (Mulligan and Berg, *Proc. Natl. Acad. Sci. USA* 78:2072-6, 1981).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR.

The cDNA sequence (or portions derived from it) or a mini gene (a cDNA with an intron and its own promoter) may be introduced into eukaryotic expression vectors by conventional techniques. These vectors are designed to permit the transcription of the cDNA eukaryotic cells by providing regulatory sequences that initiate and enhance the transcription of the cDNA and ensure its proper splicing and polyadenylation. Vectors containing the promoter and enhancer regions of the SV40 or long terminal repeat (LTR) of the Rous Sarcoma virus and polyadenylation and splicing signal from SV40 are readily available (Mulligan and Berg, *Proc. Natl. Acad. Sci. USA* 78:2072-6, 1981; Gorman et al., *Proc. Natl. Acad. Sci. USA* 78:6777-81, 1982). The level of expression of the cDNA can be manipulated with this type of vector, either by using promoters that have different activities (for example, the baculovirus pAC373 can express cDNAs at high levels in *S. frugiperda* cells (Summers and Smith, 1985, Genetically Altered Viruses and the Environment, Fields et al. (Eds.) 22:319-328, Cold Spring Harbor Laboratory Press, Cold Spring Harbor, N.Y.) or by using vectors that contain promoters amenable to modulation, for example, the glucocorticoid-responsive promoter from the mouse mammary tumor virus (Lee et al., *Nature* 294:228, 1982). The expression of the cDNA can be monitored in the recipient cells 24 to 72 hours after introduction (transient expression).

In addition, some vectors contain selectable markers such as the gpt (Mulligan and Berg, *Proc. Natl. Acad. Sci. USA* 78:2072-6, 1981) or neo (Southern and Berg, *J. Mol. Appl. Genet.* 1:327-41, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., *Mol. Cell Biol.* 1:486, 1981) or Epstein-Barr (Sugden et al., *Mol. Cell Biol.* 5:410, 1985). Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al., *J. Biol. Chem.* 253:1357, 1978).

The transfer of DNA into eukaryotic, in particular human, or other mammalian cells, is now a conventional technique. The vectors are introduced into the recipient cells as pure DNA (transfection) by, for example, precipitation with calcium phosphate (Graham and vander Eb, 1973, *Virology* 52:466) or strontium phosphate (Brash et al., *Mol. Cell. Biol.* 7:2013, 1987), electroporation (Neumann et al., *EMBO J.* 1:841, 1982), lipofection (Felgner et al., *Proc. Natl. Acad. Sci. USA* 84:7413, 1987), DEAE dextran (McCuthan et al., *J. Natl. Cancer Inst.* 41:351, 1968), microinjection (Mueller et al., *Cell* 15:579, 1978), protoplast fusion (Schather, *Proc. Natl. Acad. Sci. USA* 77:2163-7, 1980), or pellet guns (Klein et al, *Nature* 327:70., 1987). Alternatively, the cDNA can be introduced by infection with virus vectors. Systems are developed that use, for example, retroviruses (Bernstein et al., *Gen. Engrg.* 7:235, 1985), adenoviruses (Ahmad et al., *J. Virol.* 57:267, 1986), or Herpes virus (Spaete et al., *Cell* 30:295, 1982).

Using the above techniques, the expression vectors containing STLV-3 subtype D genes or cDNA sequence or fragments or variants or mutants thereof can be introduced into human cells, primate cells, mammalian cells from other species, or non-mammalian cells as desired. The choice of cell is determined by the purpose of the treatment. For example, monkey COS cells (Gluzman, *Cell* 23:175-82, 1981) that produce high levels of the SV40 T antigen and permit the replication of vectors containing the SV40 origin of replication may be used. Similarly, Chinese hamster ovary (CHO), mouse NIH 3T3 fibroblasts or human fibroblasts or lymphoblasts may be used.

Immunogenic M2e and HA peptides and carrier proteins also may be produced, for example by chemical synthesis by any of a number of manual or automated methods of synthesis known in the art. For example, solid phase peptide synthesis (SPPS) is carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotriazole or 2-(1H-benzo-triazol-1-yl)-1,1,3,3-tetramethyluronium hexafluorophosphate/hydroxybenzotriazole (HBTU/HOBT), and using p-hydroxymethylphenoxymethylpolystyrene (HMP) or Sasrin resin for carboxyl-terminus acids or Rink amide resin for carboxyl-terminus amides.

Fmoc-derivatized amino acids are prepared from the appropriate precursor amino acids by tritylation and triphenylmethanol in trifluoroacetic acid, followed by Fmoc derivitization as described by Atherton et al. *Solid Phase Peptide Synthesis*, IRL Press: Oxford, 1989.

Sasrin resin-bound peptides are cleaved using a solution of 1% TFA in dichloromethane to yield the protected peptide. Where appropriate, protected peptide precursors are cyclized between the amino- and carboxyl-termini by reaction of the amino-terminal free amine and carboxyl-terminal free acid using diphenylphosphorylazide in nascent peptides wherein the amino acid sidechains are protected.

HMP or Rink amide resin-bound products are routinely cleaved and protected sidechain-containing cyclized peptides deprotected using a solution comprised of trifluoroacetic acid (TFA), optionally also comprising water, thioanisole, and ethanedithiol, in ratios of 100:5:5:2.5, for 0.5-3 hours at room temperature.

Crude peptides are purified by preparative high pressure liquid chromatography (HPLC), for example using a Waters Delta-Pak C18 column and gradient elution with 0.1% TFA in water modified with acetonitrile. After column elution, acetonitrile is evaporated from the eluted fractions, which are then lyophilized. The identity of each product so produced and purified may be confirmed by fast atom bombardment mass spectroscopy (FABMS) or electrospray mass spectroscopy (ESMS).

The subject matter of the present disclosure is further illustrated by the following non-limiting Examples.

EXAMPLES

Example 1

Preparation of rDT/M2e Conjugate Vaccine

This example describes exemplary methods for preparing a conjugate vaccine useful in the treatment and/or inhibition of influenza infection.

Ten mg of N-succinimidyl 3-(bromoacetamido) propionate (SBAP, Pierce, Rockford, Ill.) in 40 ul DMSO were add and reacted at pH 7.2 at room temp to 28 mg of recombinant diphtheria toxin (rDT) in 2 ml buffer A (0.1 M phosphate, 1 mM EDTA, 1% glycerol, pH 7.2). The resulting solution was mixed for 4 hours. Next, the solution was applied to a SEPHADEX® G-50 column (1×50 cm) in phosphate buffered saline (PBS), and the void volume fraction (rDT-Br) was concentrated using an Amicon Ultra −15 centrifuge filter device (MILLIPORE®, Billerica, Mass.) to 2.0 ml (12.5 mg/ml); 0.2 ml was removed for analysis. To 22 mg rDT-Br in buffer A, 30 mg M2e were added in 0.2 ml NaCl and reacted at pH 7.2 overnight. The solution was then passed through a SEPHAROSE® G-75 (1×100 cm) column in PBS and the void volume fraction collected and analyzed for protein contents and molecular mass by Matrix Assisted Laser Desorption/Ionization-Time Of Flight (MALDI-TOF) mass spectrometryand sodium dodecyl sulfate polyacrylamide gel electrophoresis (SDS-PAGE) and for antigenicity by immunodiffusion.

Example 2

Characterization of Conjugate Vaccines

This example describes the characterization of the conjugate vaccines produced by the method described in Example 1.

Figure 2:
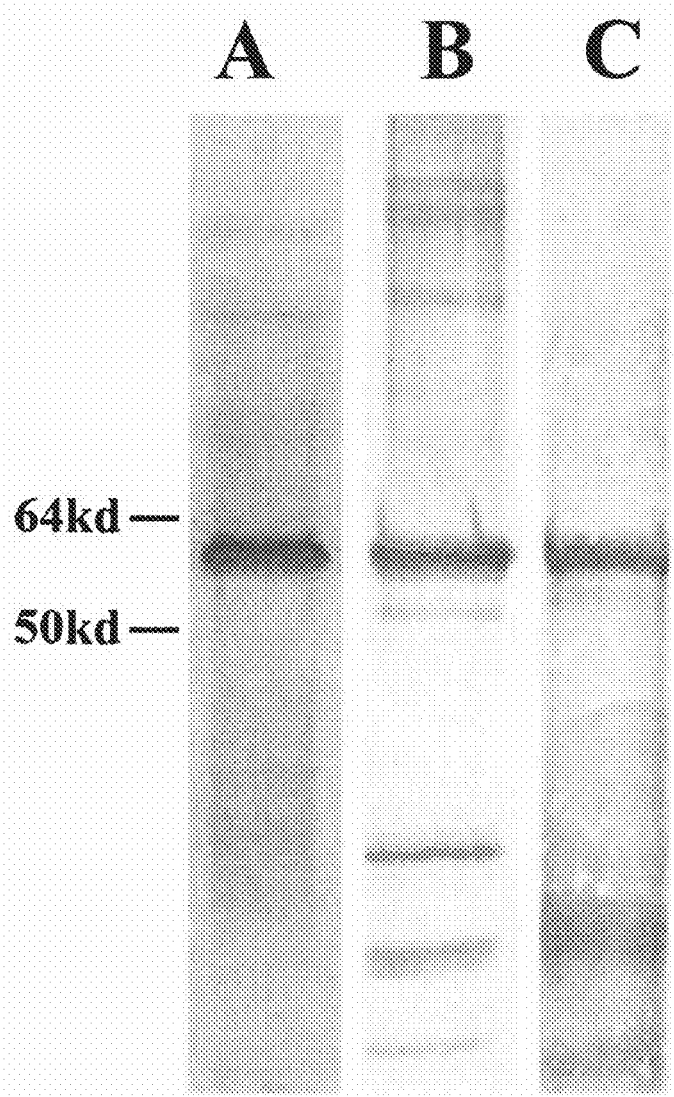
FIG. 2 is a digital image of the results of sodium dodecyl sulfate polyacrylamide gel electrophoresis (SDS-PAGE) of recombinant diphtheria toxin (rDT) (lane 1), bromoalkylated rDT (rDT-Br) (lane 2), rDT M2e peptide conjugate (rDT/M2e) lot 1 (lane 3) and rDT/M2e lot 2 (lane 4).
Figure 3:
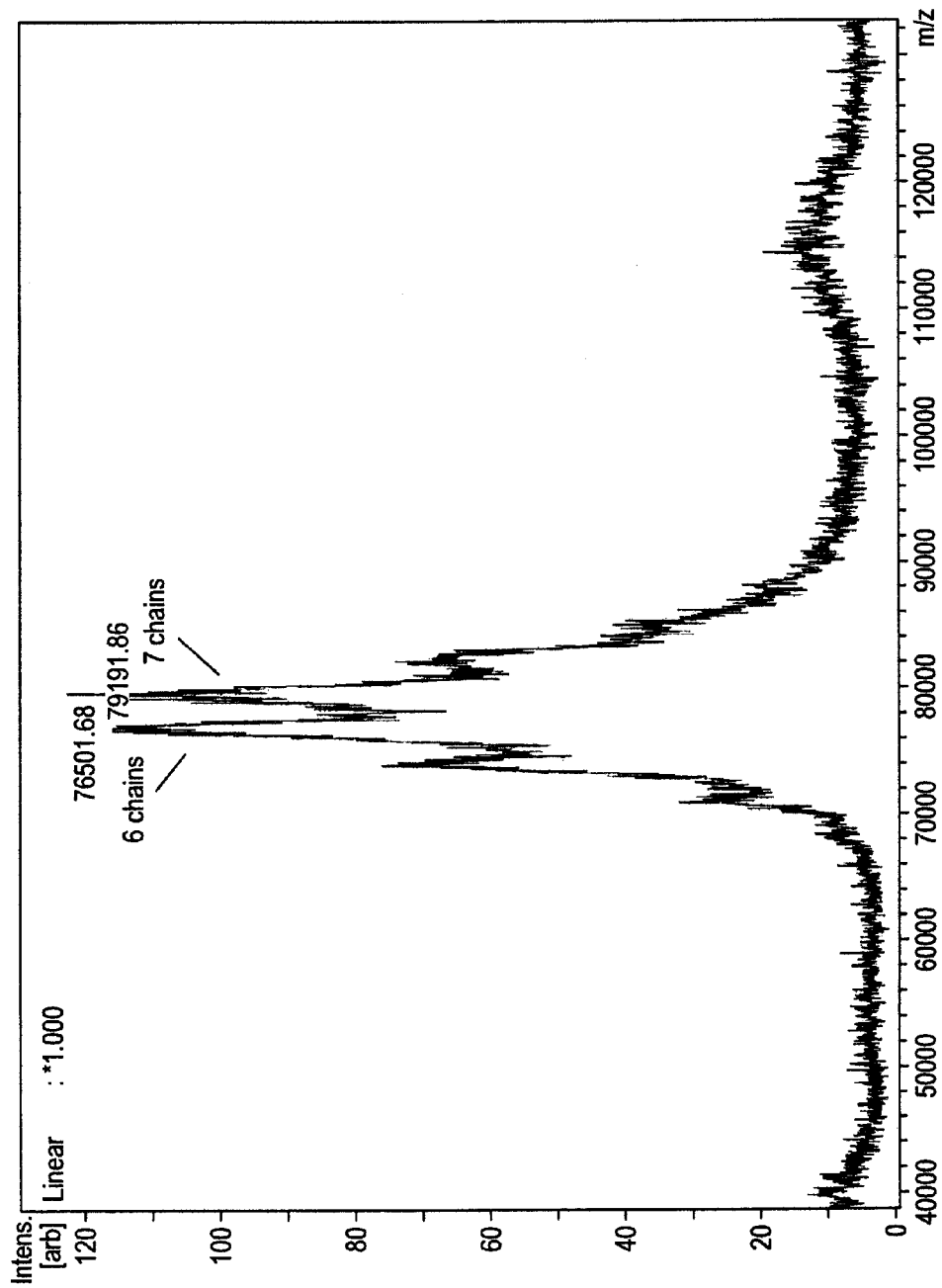
FIG. 3 is an example of a MALDI mass spectrum of rDT/M2e peptide conjugate (lot 2).
Figure 4:
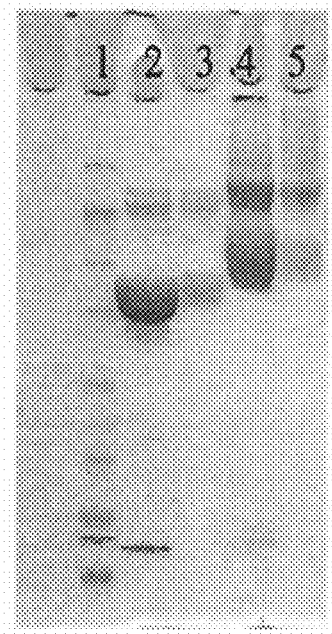
FIG. 4 is a digital image of a SDS-PAGE and Western blot analysis of recombinant hemagglutinin (HA) protein that was purified from inclusion bodies by urea solubilization and $Ni^+$-ion chelating chromatography, and refolded. Lane A: 12% SDS-PAGE, Lane B: Western blot using anti-His-tag monoclonal antibody, Lane C: Western blot using anti-H5N1 A/Vietnam/1203/2004 ferret serum.

The conjugation procedure described in Example 1 is based on formation thioether linkages between —SH group of the terminal cysteine side chain at the carboxyl end of the M2e peptide and the bromoacetyl groups attached to the side chain amino groups of the protein lysines. An average of 9-11 bromoacetyl linkers were bound to the protein (assayed by MALDI-TOF mass spectroscopy). The average molecular masses of the conjugates (lot 1 and 2) were 78 kDa indicating an incorporation of an average of 6.5 chains of M2e per rDT molecule. MALDI spectra showed species with 4-9 peptide chains per rDT molecule with the most abundant 6 and 7 chains (FIG. 2). The ratio of rDT to M2e was determined to be 1:0.28. The conjugates reacted with anti-DT and anti-M2e by an identity line and the SDS-PAGE analyses confirmed the molecular masses of conjugates (FIG. 3).

Example 3

Serology

This example describes in vivo tests of the conjugates made by the methods described in Example 1. These tests can be applied to any of the conjugate vaccines of this disclosure.

The rDT/M2e conjugate as described in Example 1 was injected subcutaneous (s.c.) as a saline solution or absorbed into alum at a dose of 2.5 µg of M2e peptide as a conjugate into NIH general purpose mice, 2 and 3 times, two weeks apart. The mice were bled 1 week after the last injection. Antibody levels were measured by ELISA and the results of two lots of rDT/M2e conjugates are presented in Table 1.

TABLE 1

Composition and Geometric Mean of serum IgG induced by M2e conjugates bound to recombinant diphtheria toxin (rDT).

| LOT | PREPARATION | No of chains | Protein:M2e ratio [wt:wt] | IgG anti-M2e [mg/ml] | | IgG anti-DT [EU] | |
|---|---|---|---|---|---|---|---|
| | | | | $2^{nd}$ inj. | $3^{rd}$ inj | $2^{nd}$ inj. | $3^{rd}$ inj. |
| 1 | DT/M2e | 6.5 | 1:0.3 | 0.04 | 1.37 | 0.07 | 29.7 |
| 1 | DT/M2e on alum | 6.5 | 1:0.3 | — | 1.4 | — | 66.2 |
| 2 | DT/M2e | 6.5 | 1:0.3 | 0.10 | 0.70 | 0.46 | 27.7 |
| 2 | DT/M2e on alum | 6.5 | 1:0.3 | 0.77 | 2.66 | 21.1 | 70.5 |
| 3 | DT/M2e on alum | 4.3 | 1:0.2 | — | 2.52 | — | 93.8 |
| 4 | DT/M2e on alum | 6.0 | 1:0.3 | — | 1.74 | — | 32.3 |

Mice (10 per group) were injected with 2.5 µg of M2e as a conjugate per mouse, 3 times, 2 weeks apart and bled one week after the last two injections.

The rDT/M2e conjugate (lot 2) was injected into ferrets to conduct a challenge study. Ten ferrets, each, were injected s.c. with 5 (Group 1) or 10 µg (Group 2) of rDT/M2e conjugate absorbed into alum, 2 ferrets with the same conjugate without alum, as a saline solution, (Group 3) and 2 ferrets with the Tris-HCl buffer only (Group 4). Ferrets were injected 3 times, 4 weeks apart. Antibody levels of the two first group's pre- (1 day before injection) and post-third injection (1 week after) are presented in Table 2. A challenge experiment in ferrets, using 100 LD50 Influenza virus strain H1N5, A/Vietnam/1203/04, showed 2/10 survival of ferrets injected with 5 µg, 3 times, alum adsorbed and 4/10 survival of ferrets injected with 10 µg, 3 times, alum adsorbed.

TABLE 2

GM of serum IgG anti-M2e levels (Elisa Units, EU) induced by conjugates of rDT/M2e bconjugate and the % of survival.

| Lot | PREPARATION | Dosage [µg/ferret] | No of animals per group | IgG anti-M2e [EU] | | % of survival |
|---|---|---|---|---|---|---|
| | | | | Pre $3^{nd}$ inj. | Post-$3^{rd}$ inj | |
| 2 | DT/M2e on alum | 5 | 10 | 41 | 61 | 20 |
| 2 | DT/M2e on alum | 10 | 10 | 37 | 87 | 40 |
| — | Tris buffer | — | 2 | na | na | 0 |

Ferrets were injected 3 times, 4 weeks apart and challenge with Influenza virus strain H1N5, A/Vietnam/1203/04 two weeks after the last injections.
Na—not analyze

Example 4

Cloning the Gene Encoding the HA Protein

This example describes cloning of an exemplary Hemagglutinin (HA) to form novel HA constructs for use in the disclosed vaccines.

An exemplary rHA construct was designed to represent the mature configuration of HA0. The amino-terminal signal sequence was removed and replaced with Met-Gly amino acid residues. NcoI and NotI restriction sites were incorporated into the construct to facilitate cloning into the pET28 protein expression vector (Novagen, San Diego, Calif.). In addition, the carboxyl terminal portion spanning viral membrane was deleted and replaced by 3× Glycine linker and six Histidine amino acid residues followed by multiple stop codons. In some examples, the gene encoding the HA protein was amplified by RT-PCR using RNA of influenza virus A/Vietnam/1203/2004 (H5N1) as a template (kindly provided by Kanta Subbarao, LID/NIAID/NIH). Viral RNA was extracted using RNAEASY® (QIAGEN®, Inc. Valencia, Calif.) according to the manufacturer's protocol. A 5 µL aliquot of RNA was amplified into a double stranded DNA fragment using SUPERSCRIPT® III ONE-STEP® (Invitrogen, Carlsbad, Calif.) following the manufacturer's protocol. The PCR sense and anti-sense primers are described below. Amplification was carried out using an ABI thermocycler programmed for 45° C. for 30 minutes, then 94° C. for 2 minutes followed by 45 cycles at 94° C. for 15 seconds, 50° C. for 30 seconds and 68° C. for 3 minutes. At the end of the 45 cycles, the run-off synthesis was carried out for 7 minutes at 68° C. The reaction mixture was then stored at 4° C. PCR primer design was based on the viral sequence data provided by the Centers for Disease Control and Prevention (CDC) for A/Vietnam/1203/2004 HA (vaccine strain CDC E2 VN1203-PR8-HA Ruben Donis, CDC, Atlanta, Ga.).

The PCR primer for the 3'-end of the HA gene produced a truncated rHA gene in which the carboxyl terminal was replaced by six histidine residues (His-6×). In addition, the design incorporated multiple translational stop codons, a Gly-Gly-Gly linker, and recognition sites for restriction enzymes MscI and NotI for cloning into the pET28 protein expression vector. The sequence encoding the His-6× tag can be removed from the expression vector using restriction enzymes MscI and NotI and replacing the gap with a MscI/NotI DNA oligonucleotide linker containing translation stop codons. In this primer, the rare ATA codon for Ile was replaced with ATT to increase protein yield when expressed. The underlined sequence is identical to the 3'-end of the negative viral RNA strand for the HA gene. The 3'-end primer was named 3HA0H5N1 (84-mer); with the sequence 5'-AAG GAA AAA AGC GGC CGC TCA TTA ATG GTG ATG ATG ATG GTG GCC ACC GCC TTG GTA AAT TCC AAT TGA TTC CAA TTT TAC TCC (SEQ ID NO: 1). The PCR primer for the 5'-end of the HA gene produced the mature rHA0 protein with the amino-terminal signal sequence removed and replaced with Met-Gly amino acid residues. In addition, the design incorporated an NcoI restriction site for cloning the DNA fragment into the pET28 expression vector. In this primer, the rare ATA codon for Ile was changed to ATT. The underlined sequence is complementary to the 5'-end of the negative strand viral RNA for the HA gene. The 5'-end primer was named 5HA0H5N1 (82-mer); with the sequence CAT GCC ATG GGT GAT CAG ATT TGC ATT GGT TAC CAT GCA AAC AAC TCG ACA GAG CAG GTC GAC ACA ATT ATG GAA AAG AAC G (SEQ ID NO: 2).

The amplified DNA fragment was purified by agarose gel electrophoresis and treated with NcoI and NotI restriction enzymes. The NcoI/NotI DNA fragment was purified by agarose gel electrophoresis and ligated into the NcoI and NotI restriction sites of the *E. coli* protein expression plasmid, pET28. The ligated plasmid was transformed into *E. coli* DH5-alpha and selected on LB-agar plates in the presence of 30 µg/ml kanamycin. Antibiotic resistant bacterial colonies were screened for plasmid inserts by direct PCR amplification using T7 promoter and T7 terminator sequencing primers and agarose gel electrophoresis. Mini-preparations of bacterial colonies containing the plasmid with the insert were sequenced for verification of the HA gene sequence by direct DNA sequencing using standard T7 promoter and T7 terminator primers and internal HA gene specific primers. One bacterial colony, which carried the pET plasmid with the correct HA gene sequence, was selected and a maxi-preparation of the plasmid, which was named pET-28HA-5, was prepared from the DH5-alpha *E. coli*. The purified pET-28HA-5 plasmid was transformed into *E. coli* BL21(DE3) Rosette II cells (Novagen) and selected on LB agar containing 30 µg/ml kanamycin and 34 µg/ml chloramphenicol. A seed stock of transformed cells was prepared and stored at −70° C. in LB media containing 50% glycerol.

Example 5

Bacterial Cell Growth and HA Protein Expression

A starter culture was grown overnight from frozen stock using Luria Bertani (LB) broth containing kanamycin and chloramphenicol at 37° C. with shaking at 250 rpm. A 7.0 liter bench top fermentor (New Brunswick Scientific, Edison, N.J.) was charged with 4 liters of modified LB media containing per liter: 10 g Bacto tryptone, 5 g Bacto yeast extract, 5 g $K_2HPO_4$, and 5 g NaCl heat sterilized for 30 minutes at 121° C. The media was allowed to cool to 37° C. and 10 ml of 1 M $MgSO_4$, 25 g glucose, 30 mg kanamycin, and 34 mg chloramphenicol per liter were added. The fermentor was inoculated with 200 ml of an overnight culture and grown at 37° C. The pH was maintained at 7.0 with the addition of 7 N $NH_4OH$, and the dissolved oxygen was maintained at 30% air saturation (using an adaptive control algorithm interfaced to a MD-Biostat system (Sartorius BBI System INC, Allentown, Pa.) by adjusting the agitation and the air flow. Protein production was induced by adding IPTG (Sigma, St. Louis, Mo.) to 1 mM final concentration when the optical density (OD600) of the culture reached 16 (4 hours). The culture continued for an additional 4 hours under the same conditions resulting in a final OD600 of 28. The total fermentor time for the vaccine lot was 8 hours. Bacteria were collected by centrifugation at 8,000 RPM and stored at −20° C. until further processing.

Example 6

Purification of the Recombinant HA

Recombinant HA in the inclusion bodies was solubilized with 6M urea, which was later removed by dialysis. Solubilized rHA was bound to a $Ni^+$-ion chelation affinity column, washed, and the rHA eluted and analyzed by SDS-PAGE and Western blotting analyses. Anti-His tag monoclonal antibody and ferret anti-H5 of a Vietnamese strain were used for detection. One hundred fifteen grams of frozen cells were collected by centrifugation from the 4-liter fermentor culture supernatant as described in Example 5 were suspended in 400 ml of "lysis buffer" (20 mM Tris-HCl pH 8.0 containing 500 mM NaCl and 5 mM immidazole) at 4° C. The cell suspension was passed twice through a cell disrupter at 9,000 psi (Manton Gaulin homogenizer, APV, NY USA). The broken cell suspension was centrifuged at 14,000 RPM for 40 minutes and the pellet, 66.5 grams, comprised of inclusion bodies with entrapped cellular debris collected and stored at −20° C. until further processing. One gram of washed inclusion bodies was resuspended in "binding buffer" (0.5 M NaCl, 20 mM Tris-HCl, 5 mM immidazole, pH 7.9) containing 6 M urea. The suspension was centrifuged at 12,000 RPM for 30 minutes to remove insoluble material and the supernatant loaded onto a 3 ml chromatography column containing chelating resin (HIS BIND® Resin Novagen) charged with $Ni^+$-ion and equilibrated with binding buffer containing 6 M urea. The column was washed extensively with binding buffer-urea followed by "washing buffer" (0.5 M NaCl, 20 mM Tris-HCl, 60 mM immidazole, pH 7.9) containing 6 M urea. The rHA was eluted with "elution buffer" (0.5 M NaCl, 20 mM Tris-HCl, 1 M immidazole, pH 7.9) containing 6 M urea and collected in 1 ml fractions. Each fraction was analyzed by SDS-PAGE, or by Western blot analysis following standard procedures known by those of ordinary skill in the art. The Western blots were developed using either anti-His tag monoclonal antibody (Novagen) or anti-H5N1 A/Vietnam/1203/2004 ferret serum (CDC, Atlanta, Ga.). Fractions containing the rHA were pooled and diluted to less than 0.1 mg/ml by slow addition of the pooled fraction to "refolding buffer" (50 mM glycine, 5 mM EDTA, 5 mM DTT, pH 9.0) using rapid stirring and a gravity-fed, 27-gauge needle attached to a 10 ml syringe barrel. The diluted solution containing the rHA was dialyzed against 3 liters of "dialysis buffer" (50 mM glycine, 5 mM EDTA, pH 9.0) with three changes. The dialyzed solution was concentrated using an AMICON® Ultra-10k 10,000 MW spin-filter (MILLIPORE® Corp. Billerica, Mass.) and the protein content of the concentrated solution determined using the bicinchoninic acid (BCA) Protein Assay reagent (Pierce, Rockford, Ill.) against a bovine serum albumin (BSA) standard. The method described in Examples 4-6 resulted in a non-glycosylated 60 kDa rHA protein of the expected characteristics as judged by polyacrylamide gel electrophoresis and Western blot analysis using anti-His tag monoclonal antibody and ferret serum against the A/Vietnam/1203/2004 virus (FIG. 4).

Example 7

Adsorption onto Alum and Treatment with Formalin

This example describes the preparation of vaccine by adsorption onto alum and/or formalin treatment Alum-adsorption and formalin treatment of rHA employed standard procedures known by those of ordinary skill in the art. ALHYDROGEL® 2% aluminum hydroxide (Brenntag Biosector, Denmark) was used to adsorb the rHA. Formalin treatment, before or after adsorption, used 25 mM lysine and 0.035% formalin. The final vaccine preparation was stored in 0.01% merthiolate at 4° C.

Example 8

Immunization of Mice

This example describes exemplary in vitro tests of the HA based vaccines.

Groups of 10 female NIH Swiss mice were injected subcutaneously with either 5 or 15 μg rHA/0.1 ml two or three times two weeks apart. Controls were injected with PBS. Blood samples were collected one week after the last immunization.

Anti-HA IgG was measured by enzyme-linked immunosorbent assay (ELISA). Nunc 96-well Flat-bottom IMMUNE® plates (Nalgene Nunc International, Rochester, N.Y.) were coated with rHA at a concentration 2 μg/ml (PBS pH 7.4) (determined by checkerboard titration) at 4° C. overnight. Antigen-coated plates were washed six times with "ELISA washing buffer" (0.14 M NaCl, 0.1% Brij 35, 0.02% NaN3) and test and control sera added in duplicates in two-fold dilutions. Following overnight incubation at room temperature, the plates were washed six times with ELISA washing buffer and anti-HA specific IgG detected using goat anti-mouse IgG conjugated to alkaline phosphatase (KPL, Gaithersburg, Md.) diluted 1:1000 in "ELISA diluent buffer" (phosphate buffered saline (PBS) pH 7.4 containing 1% bovine serum albumin (BSA) and 0.1% TWEEN®). The plates were incubated at room temperature 4 hours and washed six times with ELISA washing buffer. One hundred microliters of freshly prepared substrate (1 mg of 4-nitrophenyl phosphate disodium hexahydrate in 1 ml of "substrate buffer" (1 M Tris-HCl pH 9.8 with 3 mM $MgCl_2$) was added to each well, the enzyme-substrate reaction was carried out at room temperature for 20 minutes, and absorbance measured at 405 nm. Antibody concentration was calculated from a standard curve of pooled high responders' serum from this study and assigned a value of 100 ELISA units (EU). The results were analyzed using an ELISA data-processing program (Biostatistics and Information Management Branch, Centers for Disease Control and Prevention (CDC)) based on a four-parameter logistic-log function with a Taylor series linearization algorithm. Antibody levels are expressed as geometric means (GM) and 25th-75th percentiles.

Hemagglutination inhibition (HI) was performed by standard procedures in 96-well V bottom plates using 1% (vol/vol) horse red blood cells (HRBC). Sera were pre-treated with receptor destroying enzyme, RDE (II) "Seiken" (Denka Seiken Co., Ltd., Tokyo, Japan) from *Vibrio cholerae* (1 volume of sera: 3 volume of RDE) for 16 hours at 37° C. prior to heat inactivation for 30 minutes at 56° C. and diluted serially twofold in PBS starting at 1:10 and an equal volume of 4 HA units of virus antigen (BPL inactivated avian strain of H5 from the CDC) was added to the dilutions. After a 15 minute incubation at room temperature an equal volume of 1% (v/v) HRBC in PBS was added and the plates read after 1 hour.

The pre-immunization levels of all mice were below the detection limit. All four vaccine formulations and two dosages of rHA (5 and 15 μg) were immunogenic and induced booster responses. Alum-adsorbed rHA induced significantly higher IgG anti-rHA than the non-adsorbed preparations. Three injections of the 15 μg/mouse dose induced the highest antibody levels (449 EU). Formalin treatment by itself or before adsorption onto alum made little difference in the immune response: 40.1 vs. 61.5, 212.7 vs. 177.8; NS. However, treatment with formalin after adsorption reduced antibody levels significantly: 10 vs. 40.1, 61.5 $p=0.02$, 10 vs. 177.8, 212.7 $p<0.0001$. Among mice immunized with three 5 μg doses, groups injected with rHA-formalin-alum and rHA-alum had the highest antibody levels; GM of 212.7 and 177.8 EU, and 100% and 80% HI titer ≥40 with the Vietnam H5 influenza virus A respectively (Table 1).

Example 9

Treatment of Subjects with the Disclosed Vaccines

This example describes methods that can be used to treat a subject that has or is at risk of having an infection from influenza by administration of one or more of the disclosed vaccines. In particular examples, the method includes screening a subject having, thought to have, or at risk of having (for example due to impaired immunity, physiological status, or exposure to influenza) an influenza infection. Subjects of an unknown infection status can be examined to determine if they have an infection, for example using serological tests, physical examination, enzyme-linked immunosorbent assay (ELISA), radiological screening or other diagnostic technique known to those of ordinary skill in the art. In some examples, a subject is selected that has an influenza infection or is at risk of acquiring an influenza infection. Subjects found to (or known to) have an influenza infection and thereby treatable by administration of the disclosed vaccines are selected to receive the vaccine. Subjects may also be selected who are at risk of developing an influenza infection for example, the elderly, the immunocompromised and the very young, such as infants.

Subjects selected for treatment can be administered a therapeutic amount of disclosed vaccine. The vaccine can be administered at doses of 1 µg/kg body weight to about 1 mg/kg body weight per dose, such as 1 µg/kg body weight-100 µg/kg body weight per dose, 100 µg/kg body weight-500 µg/kg body weight per dose, or 500 µg/kg body weight-1000 µg/kg body weight per dose or even greater. However, the particular dose can be determined by a skilled clinician. The agent can be administered in several doses, for example continuously, daily, weekly, or monthly.

The mode of administration can be any used in the art. The amount of agent administered to the subject can be determined by a clinician, and may depend on the particular subject treated. Specific exemplary amounts are provided herein (but the disclosure is not limited to such doses).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An immunogenic conjugate comprising an influenza M2 ectodomain (M2e) peptide covalently linked to a carrier by a thioether linkage between a lysine amino acid residue present in carrier and a cysteine amino acid residue introduced at the C-terminal end of the M2e peptide, wherein the conjugate elicits an immune response in a subject and the average ratio of M2e peptide molecules to carrier protein molecules is between about 4:1 and 10:1.

2. The immunogenic conjugate of claim 1, wherein the carrier comprises bovine serum albumin, recombinant *B. anthracis* protective antigen, recombinant *P. aeruginosa* exotoxin A, tetanus toxoid, recombinant diphtheria toxoid, pertussis toxoid, *C. perfringens* toxoid, keyhole limpet hemocyanin, horseshoe crab hemocyanin, edestin, mammalian serum albumins, mammalian immunoglobulins, or analogs or mimetics of and combinations of two or more thereof.

3. The immunogenic conjugate of claim 2, wherein the carrier comprises recombinant diphtheria toxoid (rDT).

4. The immunogenic conjugate of claim 3, wherein the recombinant diphtheria toxoid comprises genetically detoxified diphtheria toxin wherein the histidine at position 21 is replaced with glycine (DT-H21G).

5. The immunogenic conjugate of claim 1, wherein the M2e peptide comprises the amino acid sequence set forth as $X_1LLTEVETX_2X_3X_4X_5X_6WX_7CX_8X_9X_{10}X_{11}X_{12}X_{13}X_{14}C$ (SEQ ID NO: 3), where $X_1$ can be serine or valine; $X_2$ can be proline, leucine or histidine; $X_3$ can be isoleucine or threonine; $X_4$ can be arginine or lysine; $X_5$ can be asparigine or serine; $X_6$ can be glutamic acid or glycine; $X_7$ can be glycine or glutamic acid; $X_8$ can be arginine or lysine; $X_9$ can be cysteine or tyrosine; $X_{10}$ can be glutamine or serine; $X_{11}$ can be aspartic acid or glycine; $X_{12}$ can be serine or leucine; $X_{13}$ can be serine or arginine; and $X_{14}$ can be aspartic acid or glutamic acid.

6. The immunogenic conjugate of claim 5, wherein the M2e peptide consists of the amino acid sequence set forth as $X_1LLTEVETX_2X_3X_4X_5X_6WX_7CX_8X_9X_{10}X_{11}X_{12}X_{13}X_{14}C$ (SEQ ID NO: 3), where $X_1$ can be serine or valine; $X_2$ can be proline, leucine or histidine; $X_3$ can be isoleucine or threonine; $X_4$ can be arginine or lysine; $X_5$ can be asparigine or serine; $X_6$ can be glutamic acid or glycine; $X_7$ can be glycine or glutamic acid; $X_8$ can be arginine or lysine; $X_9$ can be cysteine or tyrosine; $X_{10}$ can be glutamine or serine; $X_{11}$ can be aspartic acid or glycine; $X_{12}$ can be serine or leucine; $X_{13}$ can be serine or arginine; and $X_{14}$ can be aspartic acid or glutamic acid.

7. The immunogenic conjugate of claim 5, wherein the M2e peptide comprises the amino acid sequence set forth as SLLTEVETPTRNEWECRCSDSSDC (SEQ ID NO: 4).

8. The immunogenic conjugate of claim 7, wherein the M2e peptide consists of the amino acid sequence set forth as SLLTEVETPTRNEWECRCSDSSDC (SEQ ID NO: 4).

9. The immunogenic conjugate of claim 1, wherein the average ratio of M2e peptide molecules to carrier protein molecules is between about 4:1 and 7:1.

10. An immunogenic composition comprising the conjugate of claim 1 and a pharmaceutically acceptable carrier.

11. The immunogenic composition of claim 10, further comprising an adjuvant.

12. A method of eliciting an immune response against an influenza antigenic epitope in a subject, comprising administering to the subject the immunogenic conjugate of claim 1, thereby eliciting an immune response in the subject.

13. The method of claim 12, wherein the immune response is elicited against an influenza M2 protein.

14. A method of eliciting an immune response against an influenza antigenic epitope in a subject, comprising administering to the subject the immunogenic composition of claim 10, thereby eliciting an immune response in the subject.

15. The method of claim 14, wherein the immune response is elicited against an influenza M2 protein.

16. A method of treating and/or inhibiting an influenza infection in a subject, comprising:
   selecting a subject for treatment that has, or is at risk for developing, an influenza infection; and administering to a subject a therapeutically effective amount of the immunogenic conjugate of claim 1, thereby treating and/or inhibiting the influenza infection in a subject.

17. The immunogenic conjugate of claim 2, wherein the carrier comprises bovine serum albumin, recombinant *P. aeruginosa* exotoxin A, tetanus toxoid, recombinant diphtheria toxoid, or mammalian serum albumin.

18. The immunogenic conjugate of claim 1, wherein the average ratio of M2e peptide molecules to carrier protein molecules is between about 6:1 and 7:1.

19. An immunogenic conjugate comprising an influenza M2 ectodomain (M2e) peptide covalently linked to a carrier by a thioether linkage between a lysine amino acid residue present in carrier and a cysteine amino acid residue introduced at the C-terminal end of the M2e peptide, wherein the conjugate elicits an immune response in a subject and the M2e peptide comprises the amino acid sequence set forth as SLLTEVETPTRNEWECRCSDSSDC (SEQ ID NO: 4) and the average ratio of M2e peptide molecules to carrier protein molecules is between about 4:1 and 10:1.

20. The immunogenic conjugate of claim 19, wherein the M2e peptide consists of the amino acid sequence set forth as SLLTEVETPTRNEWECRCSDSSDC (SEQ ID NO: 4).

21. The immunogenic conjugate of claim 19, wherein the average ratio of M2e peptide molecules to carrier protein molecules is between about 6:1 and 7:1.

22. The immunogenic conjugate of claim 20, wherein the average ratio of M2e peptide molecules to carrier protein molecules is between about 6:1 and 7:1.

* * * * *